US005770720A

United States Patent [19]
Deuel et al.

[11] Patent Number: 5,770,720
[45] Date of Patent: Jun. 23, 1998

[54] UBIQUITIN CONJUGATING ENZYMES HAVING TRANSCRIPTIONAL REPRESSOR ACTIVITY

[75] Inventors: Thomas F. Deuel, Cambridge, Mass.; Zhao-Yi Wang, Millford, Conn.; Thomas E. Shenk, Princeton, N.J.

[73] Assignee: Barnes-Jewish Hospital, St. Louis, Mo.

[21] Appl. No.: 706,214

[22] Filed: Aug. 30, 1996

Related U.S. Application Data

[60] Provisional application No. 60/018,040, May 21, 1996 and provisional application No. 60/002,995, Aug. 30, 1995.

[51] Int. Cl.$^6$ .......................... C12N 9/00; C12N 15/12; C12N 15/31; C12N 15/52; C12N 15/85
[52] U.S. Cl. ...................... 536/24.5; 435/69.1; 435/69.7; 435/172.3; 435/183; 435/320.1; 435/325; 536/23.2; 536/23.5; 536/23.74
[58] Field of Search .................................. 435/375, 69.1, 435/69.7, 172.3, 183, 320.1, 325; 514/44, 23.2, 23.5, 24.5, 23.74

[56] References Cited

U.S. PATENT DOCUMENTS

| | | | |
|---|---|---|---|
| 4,215,111 | 7/1980 | Goldstein et al. | 424/177 |
| 5,108,919 | 4/1992 | Liu et al. | 435/224 |
| 5,112,767 | 5/1992 | Roy-Burman et al. | 435/320.1 |
| 5,132,213 | 7/1992 | Bachmair et al. | 435/69.7 |
| 5,156,968 | 10/1992 | Liu | 435/224 |
| 5,196,321 | 3/1993 | Bachmair et al. | 435/69.7 |
| 5,212,058 | 5/1993 | Baker et al. | 435/252.33 |
| 5,240,846 | 8/1993 | Collins et al. | 435/240.1 |
| 5,252,479 | 10/1993 | Srivastava | 435/235.1 |
| 5,262,322 | 11/1993 | Liu et al. | 435/252.33 |
| 5,358,857 | 10/1994 | Stengelin et al. | 435/69.7 |
| 5,384,255 | 1/1995 | Ciechanover et al. | 435/193 |
| 5,391,490 | 2/1995 | Varshavsky et al. | 435/224 |
| 5,399,346 | 3/1995 | Anderson et al. | 424/93.21 |
| 5,428,132 | 6/1995 | Hirsch et al. | 530/387.1 |
| 5,433,946 | 7/1995 | Allen, Jr. et al. | 424/94.3 |
| 5,459,051 | 10/1995 | Mascarenhas | 435/69.7 |
| 5,460,831 | 10/1995 | Kossovsky et al. | 424/493 |
| 5,491,064 | 2/1996 | Lichy et al. | 435/6 |
| 5,494,818 | 2/1996 | Baker et al. | 435/219 |
| 5,496,731 | 3/1996 | Xu et al. | 435/320.1 |
| 5,512,421 | 4/1996 | Burns et al. | 435/320.1 |
| 5,521,291 | 5/1996 | Curiel et al. | 530/391.7 |
| 5,543,328 | 8/1996 | McClelland et al. | 435/320.1 |
| 5,547,932 | 8/1996 | Curiel et al. | 435/65 |

FOREIGN PATENT DOCUMENTS

| | | |
|---|---|---|
| WO 94/19473 | 9/1994 | WIPO . |
| WO 95/18974 | 7/1995 | WIPO . |

OTHER PUBLICATIONS

Calkhoven CF, et al. "Multiple steps in the regulation of transcription–factor level and activity." Biochem. J. 317: 329–342, 1996.
Orkin SH, et al. "Report and Recommendations of the Panel to Assess the NIH Investments in Research on Gene Therapy.", Dec. 7, 1995.
S. Jentsch "The Ubiquitin–Conjugation System" Annu. Rev. Genct., vol. 26 (1992) pp. 179–207.
S. Jentsch et al. "The Yeast DNA Repair Gene RAD6 Encodes a Ubiquitin–Conjugating Enzyme" Nature, vol. 329 (Sep. 1987) pp. 131–134.
F. Wiebel et al. "The Pas2 Protein Essential for Peroxisome Biogenesis is Related to Ubiquitin–Conjugating Enzymes" Nature, vol. 359 (Sep. 1992) pp. 73–76.
T. Sommer et al. "A Protein Translocation Defect Linked to Ubiquitin Conjugation at the Endoplasmic Reticulum" Nature, vol. 365 (Sep. 1993) pp. 176–179.
W. Seufert "Ubiquitin–Conjugating Enzymes UBC4 and UBC5 Mediate Selective Degradation of Short–Lived and Abnormal Proteins" Eurropean Molecular Biology Organization, vol. 9, No. 2 (1990) pp. 543–550.
J. Jungmann et al. "Resistance to Cadmium Mediated by Ubiquitin–Dependent Proteolysis" Nature, vol. 361 (Jan. 28, 1993) pp. 369–371.
B. Alberts et al. "Molecular Biology of The Cell" Third Ed., Garland Publishing, Inc., NY (1994) pp. 218–222, 407, 420–426, 1283–1290.
M. Rolfe et al. "Reconstitution of p53–Ubiquitinylation Reactions From Purified Components: The Role of Human Ubiquitin–Conjugating Enzyme UBC4 and E6–Associated Protein (E6AP)" Proc. Natl. Acad. Sci. USA, vol. 92 (Apr. 1995) pp. 3264–3268.
R. Mulligan "The Basic Science of Gene Therapy" Science, vol. 260 (May 1993) pp. 926–932.
W. Seufert et al. "Role of a Ubiquitin–Conjugating Enzyme in Degradation of S– and M–Phase Cyclins" Nature, vol. 373, No. 6509 (1995) pp. 78–81.
M. Goebl et al. "The Yeast Cell Cycle Gene CDC34 Encodes a Ubiquitin–Conjugating Enzyme" Science, vol. 241, No. 4871, (1988) pp. 1331–1335.

(List continued on next page.)

Primary Examiner—Douglas W. Robinson
Assistant Examiner—Amy J. Nelson
Attorney, Agent, or Firm—Senniger, Powers, Leavitt & Roedel

[57] ABSTRACT

A human ubiquitin conjugating enzyme, designated hUBC-9, its full amino acid sequence, and nucleic acid polymers which encode hUBC-9 are disclosed. In addition to having functional ubiquitin conjugating activity, this enzyme has transcriptional repressor activity which is independent of the conjugating activity. The conjugating activity of hUBC-9 enhances transcription through degradation of transcription suppressor proteins such as WT1, and possibly, of hUBC-9 itself. The repressor activity of hUBC-9 suppress gene transcription, probably by disrupting the transcriptional initiation complex through specific interactions with the DNA binding region of the TATA binding protein (TBP). In use, hUBC-9, yUBC-9 and other ubiquitin conjugating enzymes having repressor activity can be fused to proteins having a DNA binding domain, such as Gal4, or used in conjunction with reppressors such as Wilm's tumor suppressor gene product, WT1. Such enzymes and the nucleic acid polymers encoding them can be used for regulating transcription of a target gene in both pharmaceutical and non-pharmaceutical applications.

70 Claims, 16 Drawing Sheets

OTHER PUBLICATIONS

P. Board et al. "Localization of the Human UBC Polyubiquitin Gene to Chromosome Band 12q24.3" Genomics, vol. 12 (1992) pp. 639–642.

Z–Y Wang et al. "WT1, the Wilms' Tumor Suppressor Gene Product, Represses Transcription Through an Interactive Nuclear Protein" Oncogene, vol. 10 (1995) pp. 1243–1247.

Z–Y Wang et al. "Indentification of a Single–Stranded DNA–Binding Protein That Interacts with an S1 Nuclease–Sensitive Region in the Platelet–Derived Growth Factor A–Chain Gene Promotor" J. Biol. Chem., vol. 268, No. 14 (May 1993) pp. 9172, 10681–10685.

S. Cohen et al. "Nonchromosomal Antibiotic Resistance in Bacteria Genetic Transformation of *Escherichia–Coli* by R. Factor DNA" Proc. Natl. Acad. Sci. USA, vol. 69, No. 8 (1972) pp. 2110–2114.

A. Depicker et al. "Nopaline Synthase Transcript Mapping and DNA Sequence" J. Mol. Appl. Genet., vol. 1, No. 6 (1982) pp. 561–574.

W. Dower et al. "High Efficiency Transformation of *Escherichia–Coli* by High Voltage Electroporation" Nucleic Acids Research, vol. 16, No. 13 (1988) pp. 6127–6146.

FIG. 1A

SEQ ID NO: 1

```
  1 ggatgggaag cgagcatggt gagtcctcaa gtcgcagctg ggcctgccac
 51 gtgggagtgg agggtggagg aacgtgtgga gtttcggagt ccagcccagt
101 gcgagacagc cttgaaaccg tggttggcgg gcgctccact ccgctctggg
151 ctcgaaccct gcctgaccct agctgtgccc cccactttct ccctgtctgg
201 cccctgctcc ccgccccctc acttagagga gggcacgggg aagggcaaac
251 ggtccagagg gcgggcggct gcgggctcct ctgcatcatg tgaggagggc
301 gtggggaagg acatcctggt ggggcccgat ctgggctgcc tccagcccgg
351 gcctgtgtct tggacttagt cgtggacctg gaggccagtg ccggctggc
401 cctgtcaccc tctcgctgtg acgccagcgc ctgctgactg gaggacccag
451 gttccttcgc ctgcttttc tcaggctgcc ctgaggatct gtgtttggtg
501 aaaaggagcc aaattcacct gcagggcagg cggctctagc agcttcagaa
551 gcctggtgcc ctggcgacac tggacctgcc ttggcttctt tgatcccaac
601 cccacccccg atttctgctc tgctgactgg ggaagtcatc gtgccaccca
651 gaacctgagt gcgggcctct cagagctcct tcgtccgtgg gtctgccggg
701 gactgggcct tgtctccctg gcgagtgcca ggtgaggctg cggcggctcc
751 gacgcaggtg gagctgctga cctggcccct ttctgcggct gc
```

SEQ. ID NO: 2

```
tcctccacct gtccgctacg gggaagcgcc gccgccgccg cccgctcgg          30
                                              FIG. 1A
                                              ↑
tttgaacATG TCGGGGATCG CCCTCAGCAG ACTCGCCCAG cccgagggac          80
         M  S  G  I  A  L  S  R  L  A  Q CATGGAGAA AGACCACCCA TTTGGTTTCG TGGCTGTGTCCC GAGAGGAAAG        130
 W  R  K  D  H  P  F  G  F  V  A  V  P  E  R  K  A             15

CATGGAGAA AGACCACCCA TTTGGTTTCG TGGCTGTCCC AACAAAAAAT          180
 W  R  K  D  H  P  F  G  F  V  A  V  P  T  K  N                31

CCCGATGGCA CGATGAACCT CATGAACTGG GAGTGCGCCA TTCCAGGAAA         230
 P  D  G  T  M  N  L  M  N  W  E  C  A  I  P  G  K             48

GAAAGGGACT CCGTGGGAAG GAGGCTTGTT TAAAACTACGG ATGCTTTTCA        280
 K  G  T  P  W  E  G  G  L  F  K  L  R  M  L  F  K             65

AAGATGATTA TCCATCTTCG CCACCAAAAT GTAAATTCGA ACCACCATTA         330
 D  Y  P  S  S  P  P  K  C  K  F  E  P  P  L                   81

TTTCACCCGA ATGTGTACCC TTCGGGGACA GTGTGCCTGT CCATCTTAGA         380
 F  H  P  N  V  Y  P  S  G  T  V  C  L  S  I  L  E             98

GGAGGACAAG GACTGGAGGC CAGCCATCAC AATCAAACAG ATCCTATTAG         430
 E  D  K  D  W  R  P  A  I  T  I  K  Q  I  L  L  G            115

GAATACAGGA ACTTCTAAAT GAACCAAATA TCCAAGACCC AGCTCAAGCA         480
 I  Q  E  L  L  N  E  P  N  I  Q  D  P  A  Q  A              131
```

FIG. 1C

```
GAGGCCTACA CGATTTACTG CCAAAACAGA GTGGAGTACG AGAAAAGGGT           530
 E  A  Y  T  R  I  Y  C  Q  N  R  V  E  Y  E  K  R  V           148

CCGAGCACAA GCCAAGAAGT TTGCGCCCTC ATAAgcagcg acctgtggc            580
 R  A  Q  A  K  K  F  A  P  S                                   158 atcgtcagaa ggaagggatt ggtttggcaa gaacttgttt acaacatttt           630
tgcaaatcta aagttgctcc atacaatgac tagtcacctg gggggggttgg          680 gcgggcgcca tcttccattg ccgccgcggg tgtgcggtct cgattcgctg           730
aattgcccgt ttccatacag ggtctcttcc ttcggtcttt tgtattttg            780 attgttatgt aaaactcgct tttatttaa tattgatgtc agtatttcaa            830
ctgctgtaaa attataaact tttatacttg ggtaagtccc ccaggcgagt           880
tcctcgctct gggatgcagg catgcttctc acgtgcaga gctgcacttg            930 gcctcagctg gctgtatgga aatgcaccct cccctcctgcg ctcctctcta          980 gaacctgggc tgtgctgctt ttgagcctca gaccccaggg cagcatctcg           1030
gttctgcgcc acttcctttg tgtttatatg gcgttttgtc tgtgttgctg           1080
tttaggtaaa taaactgttt atataaaaaa aaaaaaaaaa aaaaaaaaa            1130 aaaaaaa
```

FIG. 1D

SEQ ID NO:3

```
hUBC9   1 MSGIALSRLAQMEKAWRKDHPFGFVAVPTKNPDGTMNLMNWECAIPGKKG 50
            ||  |  ||  |||||||||||   ||   ||   ||    |||||
yUBC9   1 MSSLCLQRLQEERKKWRKDHPFGFYAKPVKKADGSMDLQKWEAGIPGKEG 50 hUBC9  51 TPWEGGLFKLRMLFKDDYPSSPPKCKFEPPLFHPNVYPSGTVCLSILEED 100
            |  |||||  ||| |  |||  |   ||| |||||||||||| ||||| |
yUBC9  51 TNWAGGVYPITVEYPNEYPSKPPKVKFPAGFYHPNVYPSGTICLSILNED 100 hUBC9 101 KDWRPAITIKQILLGIQELLNEPNIQDPAQAEAYTIYCQNRVEYEKRVRA 150
            ||||||||  |||  |   |    |  |          |
yUBC9 101 QDWRPAITLKQIVLGVQDLLDSPNPNSPAQEPAWRSFSRNKAEYDKKVLL 150 hUBC9 151 QAKKFAPS
            |||
yUBC9 151 QAKQYSK
```

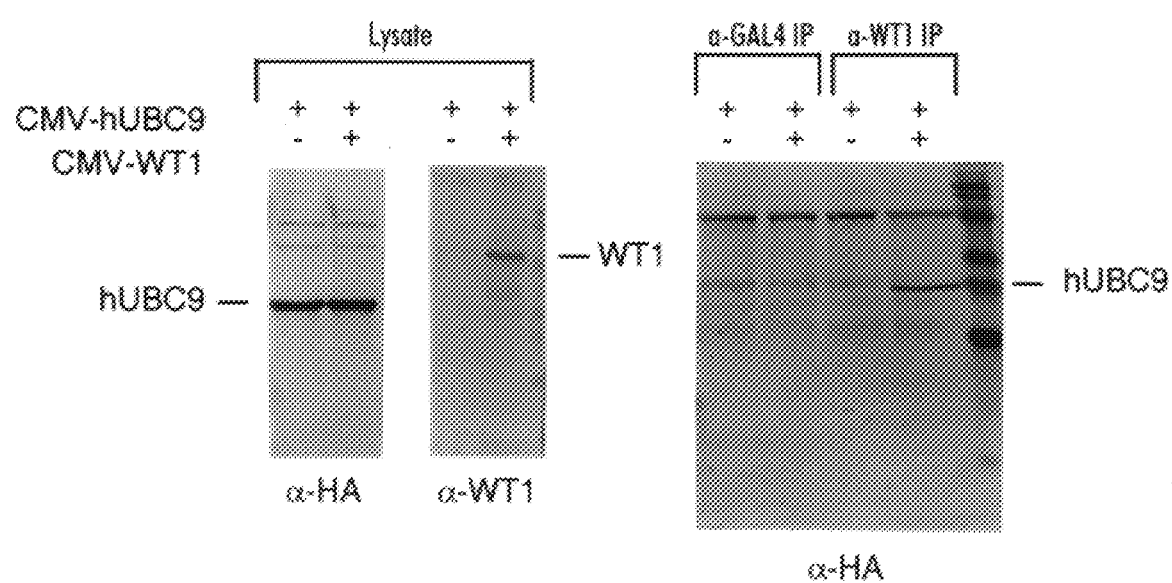

FIG. 6A
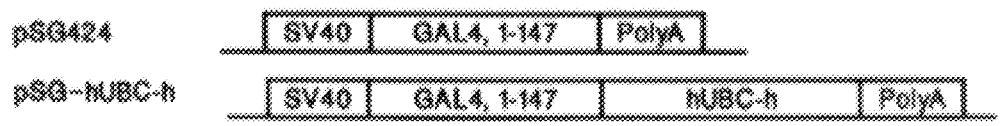
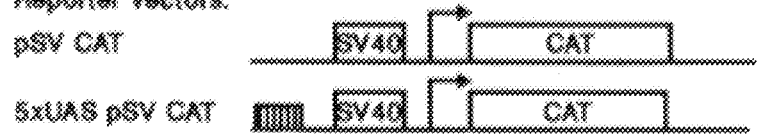
FIG. 6B
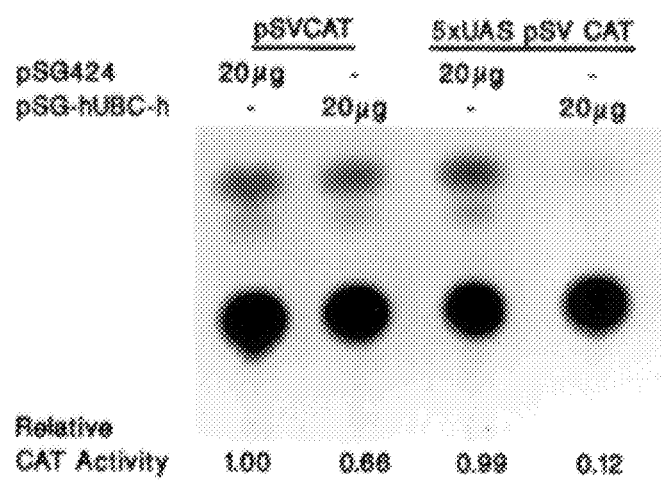

FIG. 7A
FIG. 7B
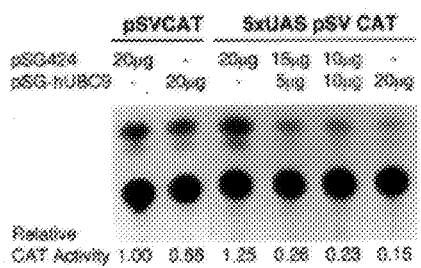
FIG. 7C
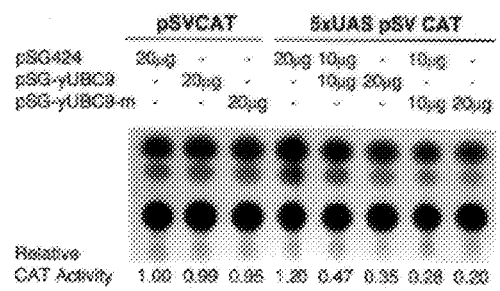

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1856 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 807..1283

( x i ) SEQUENCE DESCRIPTION: SEQ ID NO:1:

```
GGATGGGAAG  CGAGCATGGT  GAGTCCTCAA  GTCGCAGCTG  GGCCTGCCAC  GTGGGAGTGG        60

AGGGTGGAGG  AACGTGTGGA  GTTTCGGAGT  CCAGCCCAGT  GCGAGACAGC  CTTGAAACCG       120

TGGTTGGCGG  GCGCTCCACT  CCGCTCTGGG  CTCGAACCCT  GCCTGACCCT  AGCTGTGCCC       180

CCCACTTTCT  CCCTGTCTGG  CCCCTGCTCC  CCGCCCCCTC  ACTTAGAGGA  GGGCACGGGG       240

AAGGGCAAAC  GGTCCAGAGG  GCGGGCGGCT  GCGGGCTCCT  CTGCATCATG  TGAGGAGGGC       300

GTGGGGAAGG  ACATCCTGGT  GGGGCCCGAT  CTGGGCTGCC  TCCAGCCCGG  GCCTGTGTCT       360

TGGACTTAGT  CGTGGACCTG  GAGGCCAGTG  CCCGGCTGGC  CCTGTCACCC  TCTCGCTGTG       420

ACGCCAGCGC  CTGCTGACTG  GAGGACCCAG  GTTCCTTCGC  CTGCTTTTTC  TCAGGCTGCC       480

CTGAGGATCT  GTGTTTGGTG  AAAAGGAGCC  AAATTCACCT  GCAGGGCAGG  CGGCTCTAGC       540

AGCTTCAGAA  GCCTGGTGCC  CTGGCGACAC  TGGACCTGCC  TTGGCTTCTT  TGATCCCAAC       600

CCCACCCCCG  ATTTCTGCTC  TGCTGACTGG  GGAAGTCATC  GTGCCACCCA  GAACCTGAGT       660

GCGGGCCTCT  CAGAGCTCCT  TCGTCCGTGG  GTCTGCCGGG  GACTGGGCCT  TGTCTCCCTG       720

GCGAGTGCCA  GGTGAGGCTG  CGGCGGCTCC  GACGCAGGTG  GAGCTGCTGA  CCTGGCCCCT       780

TTCTGCGGCT  GCGAGGGACT  TTGAAC ATG  TCG GGG ATC  GCC CTC AGC  AGA CTC        833
                               Met Ser Gly Ile Ala Leu Ser Arg Leu
                                 1               5

GCC CAG GAG  AGG AAA GCA  TGG AGG AAA  GAC CAC CCA  TTT GGT TTC  GTG         881
Ala Gln Glu  Arg Lys Ala  Trp Arg Lys  Asp His Pro  Phe Gly Phe  Val
 10               15                    20                        25

GCT GTC CCA  ACA AAA AAT  CCC GAT GGC  ACG ATG AAC  CTC ATG AAC  TGG         929
Ala Val Pro  Thr Lys Asn  Pro Asp Gly  Thr Met Asn  Leu Met Asn  Trp
             30                        35                        40
```

|     |     |     |     |     |     |     |     |     |     |     |     |     |     |     |     | |
|---|---|---|---|---|---|---|---|---|---|---|---|---|---|---|---|---|
| GAG | TGC | GCC | ATT | CCA | GGA | AAG | AAA | GGG | ACT | CCG | TGG | GAA | GGA | GGC | TTG | 977 |
| Glu | Cys | Ala | Ile | Pro | Gly | Lys | Lys | Gly | Thr | Pro | Trp | Glu | Gly | Gly | Leu | |
|     |     |     | 45  |     |     |     |     | 50  |     |     |     |     | 55  |     |     | |
| TTT | AAA | CTA | CGG | ATG | CTT | TTC | AAA | GAT | GAT | TAT | CCA | TCT | TCG | CCA | CCA | 1025 |
| Phe | Lys | Leu | Arg | Met | Leu | Phe | Lys | Asp | Asp | Tyr | Pro | Ser | Ser | Pro | Pro | |
|     |     |     | 60  |     |     |     | 65  |     |     |     |     | 70  |     |     |     | |
| AAA | TGT | AAA | TTC | GAA | CCA | CCA | TTA | TTT | CAC | CCG | AAT | GTG | TAC | CCT | TCG | 1073 |
| Lys | Cys | Lys | Phe | Glu | Pro | Pro | Leu | Phe | His | Pro | Asn | Val | Tyr | Pro | Ser | |
|     | 75  |     |     |     |     | 80  |     |     |     |     | 85  |     |     |     |     | |
| GGG | ACA | GTG | TGC | CTG | TCC | ATC | TTA | GAG | GAG | GAC | AAG | GAC | TGG | AGG | CCA | 1121 |
| Gly | Thr | Val | Cys | Leu | Ser | Ile | Leu | Glu | Glu | Asp | Lys | Asp | Trp | Arg | Pro | |
| 90  |     |     |     |     | 95  |     |     |     |     | 100 |     |     |     |     | 105 | |
| GCC | ATC | ACA | ATC | AAA | CAG | ATC | CTA | TTA | GGA | ATA | CAG | GAA | CTT | CTA | AAT | 1169 |
| Ala | Ile | Thr | Ile | Lys | Gln | Ile | Leu | Leu | Gly | Ile | Gln | Glu | Leu | Leu | Asn | |
|     |     |     |     | 110 |     |     |     |     | 115 |     |     |     |     | 120 |     | |
| GAA | CCA | AAT | ATC | CAA | GAC | CCA | GCT | CAA | GCA | GAG | GCC | TAC | ACG | ATT | TAC | 1217 |
| Glu | Pro | Asn | Ile | Gln | Asp | Pro | Ala | Gln | Ala | Glu | Ala | Tyr | Thr | Ile | Tyr | |
|     |     |     | 125 |     |     |     |     | 130 |     |     |     |     | 135 |     |     | |
| TGC | CAA | AAC | AGA | GTG | GAG | TAC | GAG | AAA | AGG | GTC | CGA | GCA | CAA | GCC | AAG | 1265 |
| Cys | Gln | Asn | Arg | Val | Glu | Tyr | Glu | Lys | Arg | Val | Arg | Ala | Gln | Ala | Lys | |
|     |     | 140 |     |     |     |     | 145 |     |     |     |     | 150 |     |     |     | |
| AAG | TTT | GCG | CCC | TCA | TAAGCAGCGA | ACCTTGTGGCA | TCGTCAGAAG | GAAGGGATTG |     |     |     |     |     |     |     | 1320 |
| Lys | Phe | Ala | Pro | Ser | | | | | | | | | | | | |
|     | 155 |     |     |     | | | | | | | | | | | | |

| | | | | |
|---|---|---|---|---|
| GTTTGGCAAG | AACTTGTTTA | CAACATTTTT | GCAAATCTAA | AGTTGCTCCA | TACAATGACT | 1380 |
| AGTCACCTGG | GGGGGTTGGG | CGGGCGCCAT | CTTCCATTGC | CGCCGCGGGT | GTGCGGTCTC | 1440 |
| GATTCGCTGA | ATTGCCCGTT | TCCATACAGG | GTCTCTTCCT | TCGGTCTTTT | GTATTTTGA | 1500 |
| TTGTTATGTA | AAACTCGCTT | TTATTTTAAT | ATTGATGTCA | GTATTTCAAC | TGCTGTAAAA | 1560 |
| TTATAAACTT | TTATACTTGG | GTAAGTCCCC | CAGGCGAGTT | CCTCGCTCTG | GGATGCAGGC | 1620 |
| ATGCTTCTCA | CCGTGCAGAG | CTGCACTTGG | CCTCAGCTGG | CTGTATGGAA | ATGCACCCTC | 1680 |
| CCTCCTGCGC | TCCTCTCTAG | AACCTGGGCT | GTGCTGCTTT | TGAGCCTCAG | ACCCCAGGGC | 1740 |
| AGCATCTCGG | TTCTGCGCCA | CTTCCTTTGT | GTTTATATGG | CGTTTTGTCT | GTGTTGCTGT | 1800 |
| TTAGGTAAAT | AAACTGTTTA | TATAAAAAAA | AAAAAAAAAA | AAAAAAAAA | AAAAA | 1856 |

( 2 ) INFORMATION FOR SEQ ID NO:2:

( i ) SEQUENCE CHARACTERISTICS:
        ( A ) LENGTH: 1137 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 88..564

( x i ) SEQUENCE DESCRIPTION: SEQ ID NO:2:

| | | | | | |
|---|---|---|---|---|---|
| GGGAAGCGCC | GCCGCCGCCG | CCCCGCTCGG | TCCTCCACCT | GTCCGCTACG | CTCGCCGGGG | 60 |
| CTGCGGCCGC | CCCGAGGGAC | TTTGAAC ATG TCG GGG ATC GCC CTC AGC AGA | | | | 111 |
|            |            | Met Ser Gly Ile Ala Leu Ser Arg | | | |
|            |            |   1               5 | | | |

|     |     |     |     |     |     |     |     |     |     |     |     |     |     |     |     | |
|---|---|---|---|---|---|---|---|---|---|---|---|---|---|---|---|---|
| CTC | GCC | CAG | GAG | AGG | AAA | GCA | TGG | AGG | AAA | GAC | CAC | CCA | TTT | GGT | TTC | 159 |
| Leu | Ala | Gln | Glu | Arg | Lys | Ala | Trp | Arg | Lys | Asp | His | Pro | Phe | Gly | Phe | |
|     | 10  |     |     |     |     | 15  |     |     |     |     | 20  |     |     |     |     | |

| | | | | | | | | | | | | | | | | |
|---|---|---|---|---|---|---|---|---|---|---|---|---|---|---|---|---|
| GTG | GCT | GTC | CCA | ACA | AAA | AAT | CCC | GAT | GGC | ACG | ATG | AAC | CTC | ATG | AAC | 207 |
| Val | Ala | Val | Pro | Thr | Lys | Asn | Pro | Asp | Gly | Thr | Met | Asn | Leu | Met | Asn | |
| 25 | | | | 30 | | | | | 35 | | | | | | 40 | |
| TGG | GAG | TGC | GCC | ATT | CCA | GGA | AAG | AAA | GGG | ACT | CCG | TGG | GAA | GGA | GGC | 255 |
| Trp | Glu | Cys | Ala | Ile | Pro | Gly | Lys | Lys | Gly | Thr | Pro | Trp | Glu | Gly | Gly | |
| | | | | 45 | | | | | 50 | | | | | 55 | | |
| TTG | TTT | AAA | CTA | CGG | ATG | CTT | TTC | AAA | GAT | GAT | TAT | CCA | TCT | TCG | CCA | 303 |
| Leu | Phe | Lys | Leu | Arg | Met | Leu | Phe | Lys | Asp | Asp | Tyr | Pro | Ser | Ser | Pro | |
| | | | 60 | | | | | 65 | | | | | 70 | | | |
| CCA | AAA | TGT | AAA | TTC | GAA | CCA | CCA | TTA | TTT | CAC | CCG | AAT | GTG | TAC | CCT | 351 |
| Pro | Lys | Cys | Lys | Phe | Glu | Pro | Pro | Leu | Phe | His | Pro | Asn | Val | Tyr | Pro | |
| | | 75 | | | | | 80 | | | | | 85 | | | | |
| TCG | GGG | ACA | GTG | TGC | CTG | TCC | ATC | TTA | GAG | GAG | GAC | AAG | GAC | TGG | AGG | 399 |
| Ser | Gly | Thr | Val | Cys | Leu | Ser | Ile | Leu | Glu | Glu | Asp | Lys | Asp | Trp | Arg | |
| | 90 | | | | | 95 | | | | | 100 | | | | | |
| CCA | GCC | ATC | ACA | ATC | AAA | CAG | ATC | CTA | TTA | GGA | ATA | CAG | GAA | CTT | CTA | 447 |
| Pro | Ala | Ile | Thr | Ile | Lys | Gln | Ile | Leu | Leu | Gly | Ile | Gln | Glu | Leu | Leu | |
| 105 | | | | | 110 | | | | | 115 | | | | | 120 | |
| AAT | GAA | CCA | AAT | ATC | CAA | GAC | CCA | GCT | CAA | GCA | GAG | GCC | TAC | ACG | ATT | 495 |
| Asn | Glu | Pro | Asn | Ile | Gln | Asp | Pro | Ala | Gln | Ala | Glu | Ala | Tyr | Thr | Ile | |
| | | | | 125 | | | | | 130 | | | | | 135 | | |
| TAC | TGC | CAA | AAC | AGA | GTG | GAG | TAC | GAG | AAA | AGG | GTC | CGA | GCA | CAA | GCC | 543 |
| Tyr | Cys | Gln | Asn | Arg | Val | Glu | Tyr | Glu | Lys | Arg | Val | Arg | Ala | Gln | Ala | |
| | | | | 140 | | | | | 145 | | | | | 150 | | |
| AAG | AAG | TTT | GCG | CCC | TCA | TAAGCAGCGA | | CCTTGTGGCA | | TCGTCAGAAG | | | | | | 591 |
| Lys | Lys | Phe | Ala | Pro | Ser | | | | | | | | | | | |
| | | 155 | | | | | | | | | | | | | | |

| | | | | |
|---|---|---|---|---|
| GAAGGGATTG | GTTTGGCAAG | AACTTGTTTA | CAACATTTTT | GCAAATCTAA | AGTTGCTCCA | 651 |
| TACAATGACT | AGTCACCTGG | GGGGGTTGGG | CGGGCGCCAT | CTTCCATTGC | CGCCGCGGGT | 711 |
| GTGCGGTCTC | GATTCGCTGA | ATTGCCCGTT | TCCATACAGG | GTCTCTTCCT | TCGGTCTTTT | 771 |
| GTATTTTGA | TTGTTATGTA | AAACTCGCTT | TTATTTAAT | ATTGATGTCA | GTATTTCAAC | 831 |
| TGCTGTAAAA | TTATAAACTT | TTATACTTGG | GTAAGTCCCC | CAGGCGAGTT | CCTCGCTCTG | 891 |
| GGATGCAGGC | ATGCTTCTCA | CCGTGCAGAG | CTGCACTTGG | CCTCAGCTGG | CTGTATGGAA | 951 |
| ATGCACCCTC | CCTCCTGCGC | TCCTCTCTAG | AACCTGGGCT | GTGCTGCTTT | TGAGCCTCAG | 1011 |
| ACCCCAGGGC | AGCATCTCGG | TTCTGCGCCA | CTTCCTTTGT | GTTTATATGG | CGTTTTGTCT | 1071 |
| GTGTTGCTGT | TTAGGTAAAT | AAACTGTTTA | TATAAAAAAA | AAAAAAAAAA | AAAAAAAAA | 1131 |
| AAAAAA | | | | | | 1137 |

( 2 ) INFORMATION FOR SEQ ID NO:3:

( i ) SEQUENCE CHARACTERISTICS:
        ( A ) LENGTH: 158 amino acids
        ( B ) TYPE: amino acid
        ( D ) TOPOLOGY: linear ( x i ) SEQUENCE DESCRIPTION: SEQ ID NO:3:

| | | | | | | | | | | | | | | |
|---|---|---|---|---|---|---|---|---|---|---|---|---|---|---|
| Met | Ser | Gly | Ile | Ala | Leu | Ser | Arg | Leu | Ala | Gln | Glu | Arg | Lys | Ala | Trp |
| 1 | | | | 5 | | | | | 10 | | | | | 15 | |
| Arg | Lys | Asp | His | Pro | Phe | Gly | Phe | Val | Ala | Val | Pro | Thr | Lys | Asn | Pro |
| | | | 20 | | | | | 25 | | | | | 30 | | |
| Asp | Gly | Thr | Met | Asn | Leu | Met | Asn | Trp | Glu | Cys | Ala | Ile | Pro | Gly | Lys |
| | | | 35 | | | | | 40 | | | | | 45 | | |
| Lys | Gly | Thr | Pro | Trp | Glu | Gly | Gly | Leu | Phe | Lys | Leu | Arg | Met | Leu | Phe |
| | | | 50 | | | | | 55 | | | | | 60 | | |
| Lys | Asp | Asp | Tyr | Pro | Ser | Ser | Pro | Pro | Lys | Cys | Lys | Phe | Glu | Pro | Pro |

-continued

```
                65                             70                         75                            80
      Leu Phe His Pro Asn Val Tyr Pro Ser Gly Thr Val Cys Leu Ser Ile
                      85                        90                     95
      Leu Glu Glu Asp Lys Asp Trp Arg Pro Ala Ile Thr Ile Lys Gln Ile
                    100                 105                  110
      Leu Leu Gly Ile Gln Glu Leu Leu Asn Glu Pro Asn Ile Gln Asp Pro
                    115                 120                  125
      Ala Gln Ala Glu Ala Tyr Thr Ile Tyr Cys Gln Asn Arg Val Glu Tyr
                130                 135                  140
      Glu Lys Arg Val Arg Ala Gln Ala Lys Lys Phe Ala Pro Ser
      145                    150                 155
```

( 2 ) INFORMATION FOR SEQ ID NO:4:

( i ) SEQUENCE CHARACTERISTICS:
      ( A ) LENGTH: 157 amino acids
      ( B ) TYPE: amino acid
      ( D ) TOPOLOGY: linear ( x i ) SEQUENCE DESCRIPTION: SEQ ID NO:4:

```
      Met Ser Ser Leu Cys Leu Gln Arg Leu Gln Glu Glu Arg Lys Lys Trp
      1               5                   10                  15
      Arg Lys Asp His Pro Phe Gly Phe Tyr Ala Lys Pro Val Lys Lys Ala
                      20                  25                  30
      Asp Gly Ser Met Asp Leu Gln Lys Trp Glu Ala Gly Ile Pro Gly Lys
                  35                  40                  45
      Glu Gly Thr Asn Trp Ala Gly Gly Val Tyr Pro Ile Thr Val Glu Tyr
          50                  55                  60
      Pro Asn Glu Tyr Pro Ser Lys Pro Pro Lys Val Lys Phe Pro Ala Gly
      65                  70                  75                  80
      Phe Tyr His Pro Asn Val Tyr Pro Ser Gly Thr Ile Cys Leu Ser Ile
                      85                  90                  95
      Leu Asn Glu Asp Gln Asp Trp Arg Pro Ala Ile Thr Leu Lys Gln Ile
                      100                 105                 110
      Val Leu Gly Val Gln Asp Leu Leu Asp Ser Pro Asn Pro Asn Ser Pro
                  115                 120                 125
      Ala Gln Glu Pro Ala Trp Arg Ser Phe Ser Arg Asn Lys Ala Glu Tyr
                130                     135                 140
      Asp Lys Lys Val Leu Leu Gln Ala Lys Gln Tyr Ser Lys
      145                     150                 155
```

UBIQUITIN CONJUGATING ENZYMES HAVING TRANSCRIPTIONAL REPRESSOR ACTIVITY

This invention was developed, in part, through research supported by grants from the National Institute of Health (2PO1CA49712). The U.S. government may have certain rights in this invention.

The present invention claims priority to copending U.S. provisional application Ser. No. 60/002,995, filed Aug. 30, 1995, and to copending United States provisional application Ser. No. 60/018040 filed May 21, 1996.

BACKGROUND OF THE INVENTION

The present invention relates to a novel mammalian ubiquitin conjugating enzyme, and more particularly, to the identification, isolation, and purification of a human ubiquitin conjugating enzyme, the complete amino acid sequence of which has been elucidated, and to nucleotide sequences encoding the enzyme. The invention further relates to novel methods of using the enzyme and similar enzymes to regulate gene transcription and, particularly to suppress transcription of a target gene in a human and non-human host cells. In a preferred application, the invention relates to methods for enhancing the repressor activity of WT1, Wilm's tumor suppressor gene product.

Ubiquitin has been identified as playing a central role in tagging proteins for degradation, and thus in modulating their life-span in the cell. For example, nuclear proteins that are known to be regulated by ubiquitination include NFxb, cyclin B, c-jun, p53 and histones. Ubiquitin conjugating enzymes (UBCs) activate and attach ubiquitin to a protein targeted for degradation in the proteolytic proteosome pathway by transferring activated ubiquitin in thioester linkage. At least twelve separate yeast ubiquitin conjugating enzymes have been identified and sequenced. Prior to the present invention, however, only two mammalian UBCs have been identified and sequenced, and the human counterparts of yUBC-9 and other yeast UBCs have not been identified. While two yeast ubiquitin conjugating enzymes have been reported to mediate cell cycle progression, yUBC 3 (Goeble, M. G., et al. 1988) and yUBC 9 (Seufert, W. et al. 1995), ubiquitin conjugating enzymes have not heretofore been characterized as having other activities independent of their conjugating activities.

Tumor suppressor genes, such as the p53 gene, the retinoblastoma (Rb) gene and the Wilm's tumor suppressor gene, encode proteins which inhibit cell reproduction and/or transcription in various ways. For example, p53 gene protein is believed to bind to DNA and induce transcription of another regulatory gene, the product of which blocks the kinase activity of proteins important for normal cell cycle progression, thereby precluding cell replication. The Rb gene protein is thought to act by masking the activation domain of an activator protein. A Rb gene product protein and a method therapeutic use thereof are disclosed in U.S. Pat. No. 5,496,731 to Benedict et al. Gene suppressor proteins may also act in other ways, including, for example, by competing with activator proteins for specific DNA binding sites, and/or by direct or indirect interaction with the general transcription factors. Other tumor suppressor genes and gene products are disclosed in U.S. Pat. No. 5,491,064 to Howley et al. (HTS-1 gene).

The Wilm's Tumor (WT) suppressor gene product (WT1) is a bifunctional transcription factor of the Krüppel zinc-finger family. Loss of function of both alleles of the WT1 gene (11p13) is associated with some Wilm's tumors and associated syndromes. WT1 is a 52~57 kd nuclear protein which contains a glutamine/proline-rich N-terminal region and four zinc-fingers of the C2-H2 subclass in the C-terminal region. WT1 is a potent repressor of the promoter activity of several growth related genes, including the IGF-II, PDGF A-chain, CSF-1 and IGF-R promoters. WT1 has an independent repressor domain which is active when WT1 interacts with DNA through the zinc-finger domains. While the activity of repressor gene products such as WT1 is known to affect transcription, control over the biochemical mechanism by which transcriptional repression is effected is not thoroughly understood and higher levels of repression are desirable for commercial applications.

SUMMARY OF THE INVENTION

It is therefore an object of the present invention to provide a means for regulating transcription in cells, and particularly, a means for suppressing transcription of a target gene in a host cell. It is also an object of the invention to enhance the repressor activity of known repressor proteins such as WT1, Wilm's tumor suppressor gene product.

The present invention, therefore, is directed to a novel, isolated and substantially purified mammalian ubiquitin conjugating enzyme, hUBC-9, having a molecular weight of about 16 kilodaltons to about 18 kilodaltons, preferably about 17 kilodaltons, a sequence length of from about 150 to 165 amino acid residues, preferably 158 amino acid residues, and having conjugating activity and/or transcriptional repressor activity. The present invention is also directed to a protein having an amino acid sequence which includes the amino acid sequence of hUBC-9, SEQ ID NO: 3. The invention is directed as well to a protein which has ubiquitin conjugating activity or transcriptional repressor activity and which includes a portion of the amino acid sequence of hUBC-9, SEQ ID NO: 3, at least about 12 amino acid residues in length. The included portion of the hUBC-9 sequence confers the conjugating activity or the repressor activity on the protein. The invention is directed to proteins which have transcriptional repressor activity and have at least about 60% sequence identity to hUBC-9, SEQ ID NO: 3, more preferably at least about 65% sequence identity, more preferably at least about 75% sequence identity, more preferably at least about 85% sequence identity and most preferably at least about 95% sequence identity to hUBC-9. A $C^{93}$ mutant of hUBC-9, which does not have ubiquitin conjugating activity, but retains its transcriptional repressor activity, is a particularly preferred protein.

The invention is directed, moreover, to substantially isolated nucleic acid polymers encoding hUBC-9. The nucleic acid polymer preferably has a nucleic acid sequence selected from the group consisting of: (a) SEQ ID NO: 1; (b) SEQ ID NO: 2; (c) a nucleic acid sequence which includes the nucleic acid residues defined by the sequence from position 88 to position 564 of SEQ ID NO: 2. The invention is also directed to a substantially isolated nucleic acid polymer which encodes a protein having ubiquitin conjugating activity or transcriptional repressor activity and having an amino acid sequence which includes a portion of the amino acid sequence of hUBC-9, SEQ ID NO: 3. The included portion is at least about a 12 amino acid residues in length and confers the conjugating activity or the repressor activity on the protein. The invention is directed to a nucleic acid polymer which is at least about 36 nucleic acid residues in length and which encodes a protein which has transcriptional repressor activity. Such a nucleic acid fragment can encode a protein which has at least about 60% sequence identity to hUBC-9SEQ ID NO: 3, or alternatively, can hybridize to a nucleic acid polymer which is complementary to the aforementioned nucleic acid polymers which constitute a part of the invention. The invention is also directed to nucleic acid polymers which are complementary to the aforementioned nucleic acid polymers of the invention.

The invention is directed as well to methods for producing hUBC-9 or a segment thereof using a host cell transfected with a vector having a DNA which encodes hUBC-9 or a segment thereof. The method preferably comprises producing a plasmid vector having DNA (including genomic DNA and/or genomic DNA). The DNA encodes the aforementioned hUBC-9 protein or a segment or homolog thereof. The plasmid vector is transfected into a host cell and hUBC-9 is expressed in the host cell. If desired, the expressed hUBC-9 may be purified from the host cell. The invention is also directed to the vector and to the host cell transfected therewith.

The invention is further directed to a host cell co-transfected with first and second plasmid vectors each comprising DNA. The DNA of the first vector comprises a nucleic acid polymer which encodes a transcriptional repressor protein other than a UBC-9 protein, including for example, WT1. The DNA of the second vector comprises a nucleic acid polymer which encodes an adapter protein having transcriptional repressor activity which is preferably independent of the transcriptional repressor activity of the transcriptional repressor protein. The adapter protein associates or interacts with the transcriptional repressor protein after both are co-expressed in the host cell. The adapter protein has an amino acid sequence which includes a portion of the amino acid sequence of a ubiquitin conjugating enzyme that has transcriptional repressor activity. Exemplary ubiquitin conjugating enzymes include hUBC-9, yUBC-9, other members of the UBC-9 family and other ubiquitin conjugating enzymes. The included portion of the amino acid sequence is at least about 12 amino acid residues in length.

The invention is directed, moreover, to a fusion protein comprising a transcriptional repressor domain and a DNA binding domain. The transcriptional repressor domain has an amino acid sequence which includes at least a 12 amino acid residue portion of the amino acid sequence of a ubiquitin conjugating enzyme that has transcriptional repressor activity. The DNA binding domain is preferably a domain which binds sufficiently close to a promoter region of a target gene to allow the ubiquitin conjugating enzyme to repress transcription. Exemplary DNA binding domains include Gal4, LexA and any of the zinc-finger domains. The invention also relates to nucleic acid polymers encoding such a fusion protein, plasmid vectors comprising such nucleic acid polymers and to host cells transformed therewith. The invention is directed as well to a method for producing a fusion protein having a transcriptional repressor domain and a DNA-binding domain. The method comprises: producing a plasmid vector comprising DNA which encodes the fusion protein described above, transfecting the plasmid vector into a host cell, expressing the fusion protein in the host cell, and, if desired, purifying the expressed fusion protein from the host cell.

In another aspect, the invention is directed to a composition comprising a protein having transcriptional repressor activity and an acceptable carrier, diluent or biochemical delivery agent suitable for introducing the protein into a target cell. The protein has transcriptional repressor activity and has an amino acid sequence which includes at least a 12 amino-acid residue long portion of a ubiquitin conjugating enzyme which has transcriptional repressor activity. The protein derives its transcriptional repressor activity from the included portion of the enzyme. The composition can be used for non-pharmaceutical (ie, non-human) uses, but can also be a pharmaceutical composition, in which the aforementioned protein is combined with a pharmaceutically acceptable carrier, diluent and/or gene therapy delivery agent.

The invention is further directed to a composition suitable for use in introducing a nucleic acid polymer to a cell, whereby the expression product of the nucleic acid polymer is exposed to and/or contacts a target gene therein. The composition can be used for pharmaceutical or non-pharmaceutical applications to regulate transcription. The composition comprises a nucleic acid polymer and a gene therapy delivery agent. When used in a pharmaceutical application, the amount of the nucleic acid polymer or construct containing the same is sufficient to, upon expression in a host cell, express a pharmaceutically effective amount of the protein to regulate a target gene in the cell. The nucleic acid polymer is used in conjunction with a pharmaceutically acceptable gene therapy delivery agent. The nucleic acid polymer encodes a protein having transcriptional repressor activity and having an amino acid sequence which includes at least a 12 amino-acid residue long portion of a ubiquitin conjugating enzyme which has transcriptional repressor activity. The included portion of the enzyme confers the repressor activity on the protein. The nucleic acid polymer can, alternatively, have a nucleic acid sequence which is complementary to the aforementioned nucleic acid polymers of the composition. The nucleic acid composition can be a virus which has a viral genome that includes the nucleic acid polymer being delivered to the target gene. The ubiquitin conjugating enzyme used in such a composition is preferably a UBC-9 protein such as hUBC-9, yUBC-9 or yUBC-9-m. Another pharmaceutical composition comprises a pharmaceutically active amount of the fusion protein set out above and a pharmaceutically acceptable carrier.

The invention is also directed to a method of regulating transcription of a target gene in a cell. The method comprises exposing the target gene to and/or contacting the target gene with a protein having transcriptional repressor activity. The protein has an amino acid sequence which includes at least a 12 amino acid residue portion of the amino acid sequence of a ubiquitin conjugating enzyme having transcriptional repressor activity, such as a UBC-9. A composition which includes the protein or which includes a nucleic acid polymer encoding the protein may be introduced into the cells in a number of ways, including by contacting, infecting or transfecting the target cells with a gene therapy delivery agent such as a virus. The amount of protein to which the gene is exposed is more than the endogenous amount normally present within the cell. The cell can be an eukaryotic cell such as a fungal cell (e.g. a yeast cell), a plant cell, a non-human animal or mammalian cell or a human cell. The cell can also be a cell which has been infected with a virus wherein the viral genome is exposed to the transcription regulating protein. The invention is also directed to method of modulating neoplastic tissue growth. In the method, neoplastic tissue cells are contacted with a neoplastic-tissue-growth-modulating amount of one of the pharmaceutical compositions set forth above, thereby modulating the growth of the neoplastic tissue. The invention relates as well to a method of inhibiting the proliferation of Wilm's tumor cells. The method comprises introducing into Wilm's tumor cells a Wilm's-tumor-inhibiting amount of a ubiquitin conjugating enzyme or a segment thereof having transcriptional repressor activity, or alternatively, introducing a nucleic acid polymer which encodes such an amount of the enzyme, and preferably co-expressing WT1 therewith.

The discoveries described herein provide an important analytical tool for, and a critical link in the development of methods by which transcriptional repressors or promoters may be made to either inhibit or enhance a variety of cell activities in a desired manner. hUBC-9 and other members or the UBC-9 family can be used, for example, in chemotherapy, gene therapy and drug development. Other uses of the invention include its use to regulate the rate of both specific and general gene transcription and the cell cycle, including the control of abnormal expression of genes associated with human disease such as those caused by virus, or associated with yeast infections. The invention has use in non-pharmaceutical applications in the yeast, baking and brewing industries, and also in conjunction with enzymatic conversion methods for producing valuable chemical commodities such as essential amino acids. The enzyme, its activities and other features, methods of expressing the enzyme, and methods for its use are described in greater detail below.

Other features and objects of the present invention will be in part apparent to those skilled in the art and in part pointed out hereinafter.

BRIEF DESCRIPTION OF THE DRAWINGS

The invention is further disclosed and illustrated by the accompanying figures. In the earlier U.S. provisional applications from which the present invention claims priority, and in the figures therein, other designations were used to refer to the enzyme hUBC-9. Specifically, the enzyme has been heretofore referred to using the acronym "TRA", "human UBC," and/or hUBC-h. The present terminology, hUBC-9, has been incorporated to be consistent with the literature. However, each of these designations refers to the same enzyme, hUBC-9, shown in FIG. 1B and also depicted in FIG. 1A as corresponding to certain nucleotide sequences shown in FIG. 1A.

FIGS. 1A and 1B show nucleotide and amino acid sequences for hUBC-9. FIG. 1A shows the full length nucleotide sequences (SEQ ID NO: 1 and SEQ ID NO: 2) and the predicted amino acid sequence (SEQ ID NO: 3) for two cDNA clones encoding hUBC-9. The vertical line connecting the cytosine at position 792 of the longer form and at position 73 of the shorter form indicates the splice site and origin of common nucleotide sequences of the two alternative spliced mRNA. FIG. 1B shows a comparison of predicted amino acid sequences of hUBC-9 (SEQ ID NO: 3) and yUBC-9(SEQ ID NO: 4).

FIG. 2A shows Northern blot of hUBC-9 in different human tissues. FIG. 2B shows Southern blot analysis of the hUBC-9 gene.

FIGS. 3A and 3B show in vitro binding of WT1 and hUBC-9, in Western blot analyses of associated WT1 and hUBC-9 proteins. FIG. 3A shows blots of eluates taken from matrix-coupled GST-hUBC-9 which had been passed over and incubated with WT1 from 293 cell extracts. FIG. 3B shows the results of co-immunoprecipitation of WT1 and hUBC-9 from 293 cells co-transfected with WT1 and HA-tagged hUBC-9 expression vectors.

FIG. 5A shows the relative CAT activity when various amounts of WT1 and hUBC-9 expression vectors are co-transfected. FIG. 5B illustrates the relative CAT activity of independent assays at different times±standard deviation of each.

FIGS. 6A and 6B show the transcriptional repressor activity of a hUBC-9/Gal4 DNA binding domain fusion protein. FIG. 6A shows the expression and reporter vector constructs. FIG. 6B shows the relative CAT activity.

FIGS. 7A–7C show the transcriptional repressor activity of hUBC-9, yUBC-9, and yUBC-9-m/Gal4 DNA binding domain fusion proteins. FIG. 7A shows the expression and reporter vector constructs. FIG. 7B shows the relative CAT activity for hUBC-9/Gal4 fusion proteins. FIG. 7C shows the relative CAT activity for yUBC-9/Gal4 and yUBC-9-m/Gal4 fusion proteins.

FIG. 9B shows the blots resulting from the various GST/hUBC-9 capture assays.

FIG. 11A shows the results of assays using hUBC-9 and an end-labeled DNA probe containing the TATA box either (a) without TBP present (columns A1–A3), (b) with TBP present but without TFIIB present (columns B1–B3) and (c) with both TBP and TFIIB present (columns C1–C3). FIG. 11B shows the results of similar assays in which TBP was present with varying amounts of hUBC-9.

FIG. 12A shows the relative level of expression of the reporter vector for assays where a GAL4/hUBC-9 fusion protein (pSGhUBC-9) (0 or 10 μg), TBP (0, 0.5 or 2.5 μg) and/or TFIIB (5 μg) were co-expressed in 293 cells in varying combinations. FIG. 12B shows the relative level of expression of the reporter vector where a mutant TBP, TBPΔ1-138 (0, 2.5 and 5 μg), and the hUBC-9/Gal4 fusion protein (0, 10 μg) were co-expressed in various combinations.

DETAILED DESCRIPTION OF THE INVENTION

Figure 2A:
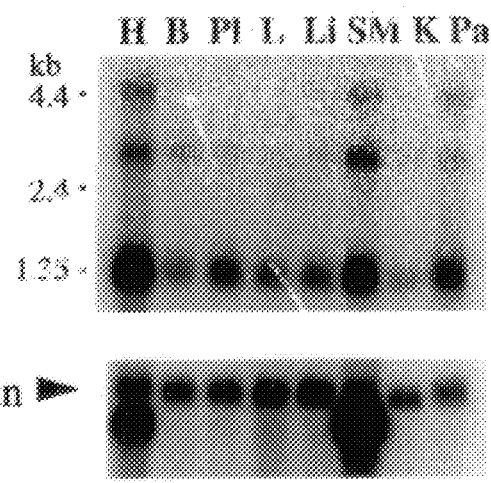
FIGS. 2A and 2B show the results of Northern and Southern blot analyses, respectively.

As used herein, the various symbols for amino acids are as set forth in Table 1.

TABLE 1

Amino Acid Abbreviations

| A | Ala | Alanine |
|---|---|---|
| B | Asx | Asparagine or aspartic acid |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| Z | Glx | Glutamine or glutamic acid |

As used herein, a "substantially purified" protein means that the protein is separated from a majority of host cell proteins normally associated with it or that the protein is synthesized in substantially purified form, such synthesis including expression of the protein in a host cell from a nucleic acid polymer exogenously introduced into the cell by any suitable gene-therapy delivery means. A "substantially isolated" nucleic acid polymer means that the mixture which comprises the nucleic acid polymer of interest is essentially free of a majority of other nucleic acid polymers normally associated with it. A "nucleic acid polymer" includes a polymer of nucleotides or nucleotide derivatives or analogs, including for example deoxyribonucleotides, ribonucleotides, etc. Genomic DNA, cDNA and mRNA are exemplary nucleic acid polymers. The term "regulate transcription" is intended to include enhancement and/or repression of transcription. The term "gene" is intended to include both endogenous and heterologous genes, and specifically, both genomic DNA which encodes a target protein in a naturally occurring cell, and also cDNA encoding the target protein, wherein the CDNA is a part of a nucleic acid construct such as a plasmid vector or virus which has been introduced into a cell. The contents of each of the references cited herein are being incorporated by reference in their entirety.

The present invention relates to newly discovered human ubiquitin conjugating enzymes, designated hUBC-9, which in addition to having a functional conjugating activity, have an independent transcriptional repressor activity. Both the conjugating and the repressor activities have been found to influence transcription. The conjugating activity of hUBC-9 enhances transcription through degradation of transcription suppressor proteins such as WT1, and possibly, of hUBC-9 itself. The repressor activity of hUBC-9 represses transcription independently of the conjugating activity. For example, hUBC-9 strikingly enhances the function of WT1 as a repressor of gene transcription. The enzyme also acts independently of WT1 to suppress gene transcription itself, particularly when fused to proteins having a DNA binding domain, such as Gal4.

While not being bound to a particular theory, UBC-9 acts as a potent repressor by disrupting the transcriptional initiation complex through specific interactions with the DNA binding region of the TATA binding protein (TBP). Such interactions are concentration dependent and result in destabilized TPB/DNA interactions and interference with formation of the TFIIB/TBP transcription initiation complex. Moreover, hUBC-9 can operate in conjunction with other proteins having a repressor effect, such as WT1, to result in a combined repressor effect which is enhanced relative to the repressor effect of WT1 alone or of hUBC-9 alone. Hence, the association of hUBC-9 with other repressor proteins, either through protein-protein interactions as with WT1 or by positioning hUBC-9 in the vicinity of the promoter as a fusion protein comprising hUBC-9 and a DNA binding domain, such as the domain of Gal4, Lex A, zinc-fingers or others. DNA binding proteins which are fused to hUBC-9 or repressor proteins which specifically interact with hUBC-9 appear to position human UBC-9 to an appropriate site in relation to promoter DNA such that hUBC-9 can interact with the TBP, and thereby reduce transcription initiation. Moreover, in the combined WT1/hUBC-9 system, the conjugating activity of hUBC-9 appears to operate in conjunction with hUBC-9's repressor activity by regulating the levels of WT1 present in the system. Such regulation of WT1 levels is accomplished through its ubiquitin conjugating activity and the associated ubiquitin-dependent proteolytic pathway. Moreover, the ubiquitin conjugating activity of hUBC-9 and its repressor activity may act at the same time, with hUBC-9 interacting simultaneously with WT1 (via its conjugating activity) and with the TBP (via its repressor activity). hUBC-9 may also interact with other repressors such as p53 and Rb in a similar manner. Advantageously, inhibition of UBC-9's conjugating activity results in even a greater degree of repression of the transcription initiative.

Moreover, the homologous ubiquitin conjugating enzymes of other eukaryotes, such as yeast (yUBC-9), exhibit the same bifunctional activities as hUBC-9: transcription repression and ubiquitin conjugation. The highly conserved nature of UBC-9 among species, both in amino acid sequence and in function, suggests a universal role for this family of proteins. Accordingly, many facets of the invention are directed to the family of proteins which are structurally homologous and functionally equivalent to hUBC-9, this family being collectively referred to herein using the designation UBC-9. UBC-9 includes any such proteins whether they are identified herein or discovered in the future. Aspects of the invention which relate to individual species' proteins are designated herein as hUBC-9 for humans and yUBC-9 for yeast. Many facets of the invention also relate to other ubiquitin conjugating enzymes other than the UBC-9 enzymes, provided, that such ubiquitin conjugating enzymes have transcriptional repressor activity in addition to their conjugating activity.

The several aspects of the present invention, including the hUBC-9 protein and nucleic acid polymers which encode it, the transcriptional repressor activity of ubiquitin conjugating enzymes such as a UBC-9 enzyme, and the interaction between UBC-9 enzymes and other transcription repressor proteins, especially such proteins having a DNA binding domain, and in particular tumor suppressor proteins such as WT1, collectively enable several practical applications, including both pharmaceutical applications involving humans and non-pharmaceutical uses.

hUBC-9

A yeast two hybrid system was used to identify clones encoding the human ubiquitin conjugating (UBC) enzyme of the present invention. (Example 1). FIG. 1A shows the complete nucleotide sequences of two independent cDNA clones, designated as SEQ ID NO: 1 and SEQ ID NO: 2, which were established from two alternatively spliced mRNAs. The cDNA clones both encode hUBC-9. The amino acid product resulting from transcription and translation of these cDNA clones migrated identically in SDS-containing polyacrylamide gel as a 17 kilodalton protein.

hUBC-9 has the amino acid sequence set forth in SEQ ID NO: 3 and shown in FIG. 1B. Based on a comparison with data in Genebank, hUBC-9 is an active human (h) homolog of the yeast ubiquitin conjugating enzyme-9, yUBC-9 or E2, the intermediate enzyme in the ubiquitin protein degradation pathway. The human UBC-9 sequence has a 56% amino acid identity overall with yUBC-9, including identical sequences of 9 amino acids in separate regions. The 158 amino acid sequence of hUBC-9 also contains a cysteine residue in precise alignment with the active site cysteine of yeast UBC-9 (boxed, FIG. 1B).

Figure 3A:
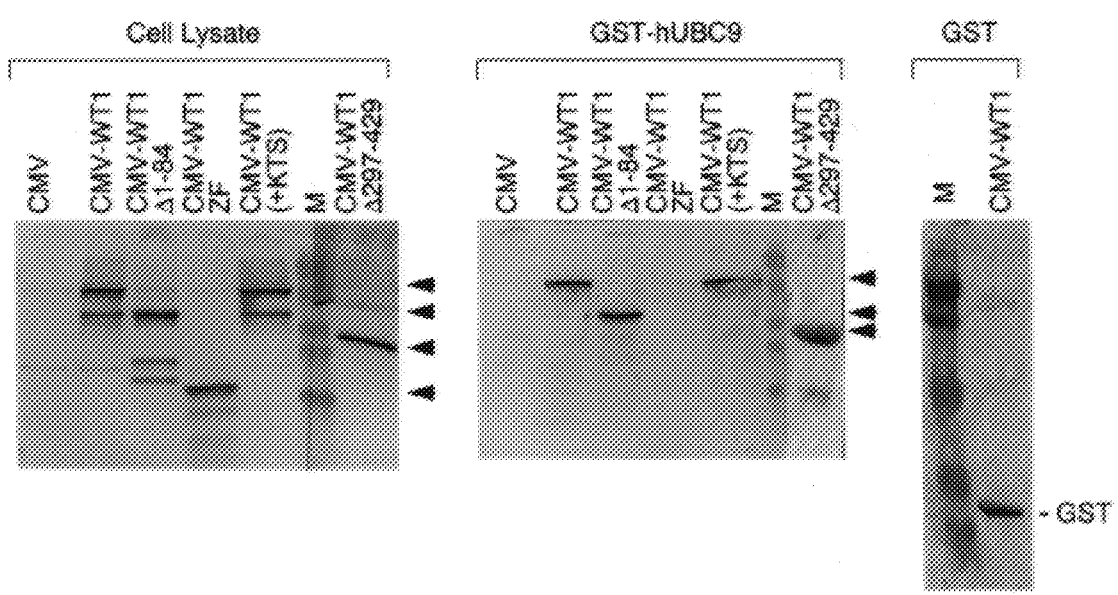
Figure 8:
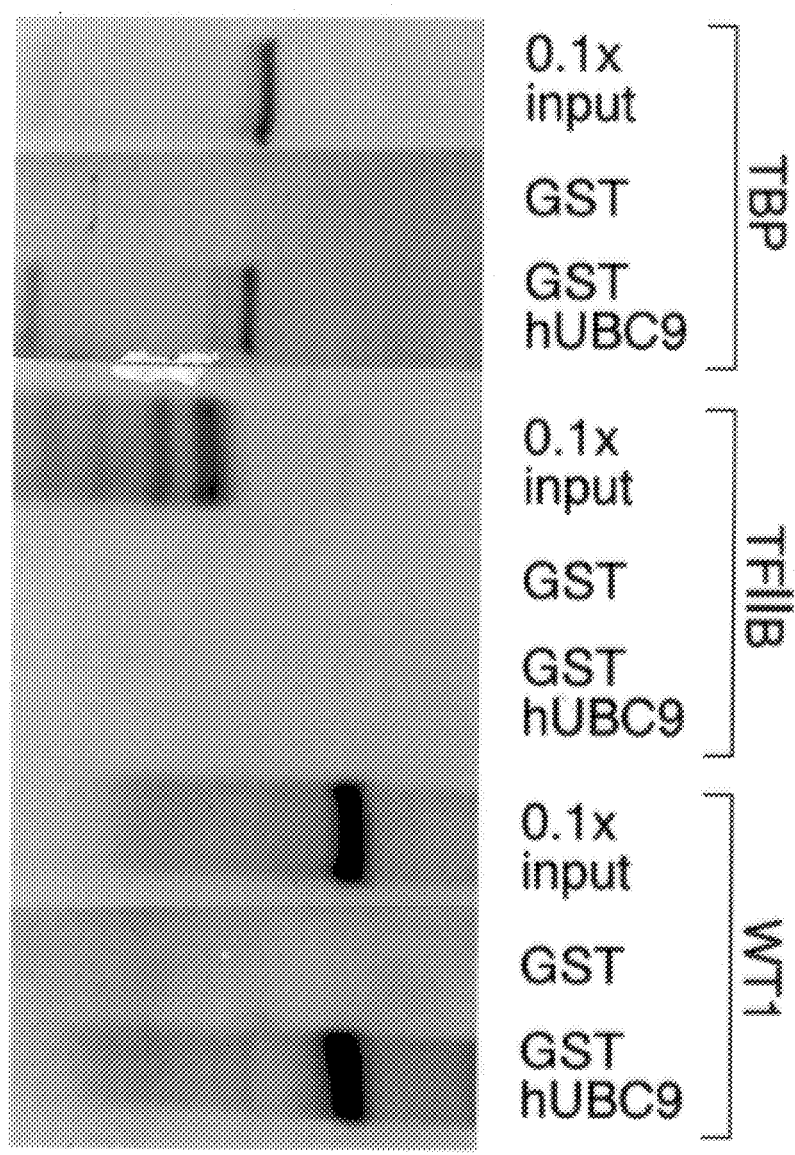
FIG. 8 shows the results of GST/hUBC-9 capture assays for TATA binding protein (TBP), transcription factor IIB (TFIIB) and Wilm's tumor suppressor gene product, WT1.
Figure 9A:
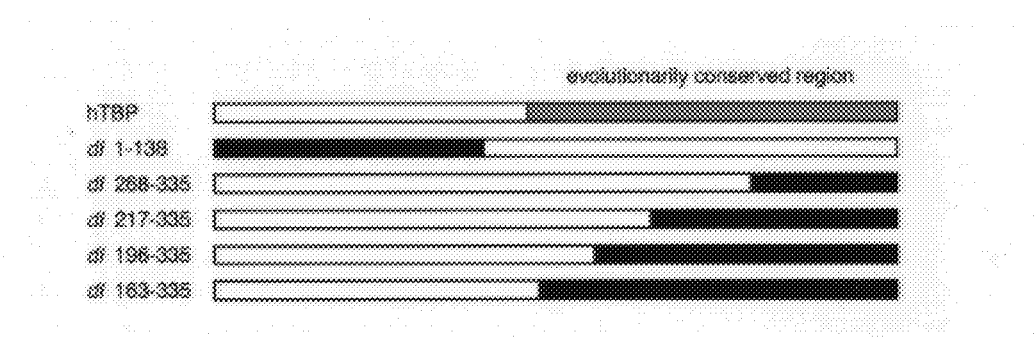
FIGS. 9A and 9B relate to GST/hUBC-9 capture assays with wild type hTBP and with several mutant TATA binding proteins, mTBP. In the schematic representations in FIG. 9A, the shaded area of the wild-type hTBP represents the highly conserved region between species. The shaded area for the mutant TBP's represents the portion of the TBP deleted. The term "dl x–y" indicates that in the mTBP, residues x through y were deleted.
Figure 9B:
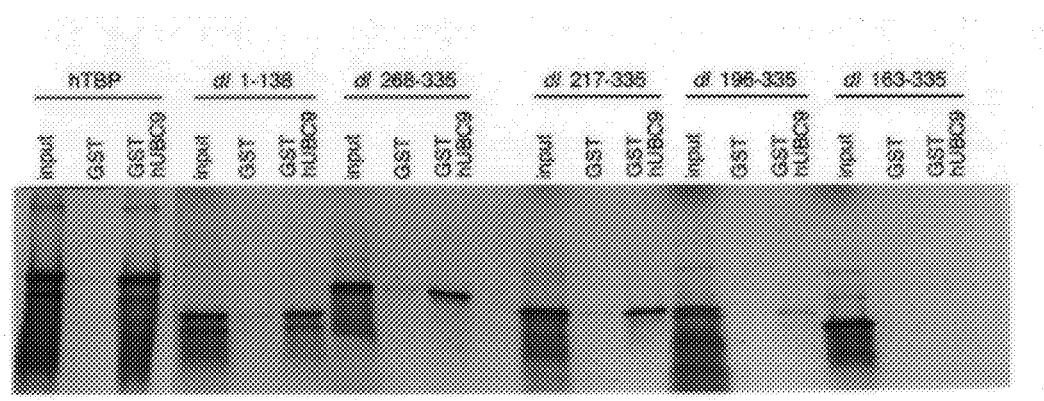

Human UBC was expressed in a all human tissues tested, including heart, brain, placenta, lung, smooth muscle, kidney and pancreas tissues. (Example 2). However, the level of expression varied in different tissues, as demonstrated by the results of a Northern blot experiment shown in FIG. 2A. Northern blots of hUBC-9 in different tissues resulted in generally strong hybridization signals of 2.8 and 1.3 kb. However, heart and smooth muscle are seen to express significantly higher levels of transcripts relative to other tissues analyzed, and kidneys appear to express relatively less of the 2.8 kb mRNA isoform.

hUBC-9 is encoded by a single gene, as demonstrated by experiments in which Southern blots of human genomic DNA were digested with different restriction enzymes and probed with the 1.1 kb fragment of hUBC-9 cDNA. (Example 3). Single hybridization signals were seen in digests of PstI and BamHI (FIG. 2B), suggesting that the human UBC gene exists as a single copy gene in the human genome.

hUBC-9 is further characterized by its association with the repressor domain of the Wilm's tumor suppressor gene product, WT1. Human UBC binds to WT1 both in vivo and in vitro. Protein-protein interactions between hUBC-9 and WT1 were initially demonstrated in the yeast two hybrid system by high levels of β-galactosidase activity, as shown in Table 1. (Example 1). Additional experiments were carried out to confirm the WT1-human UBC protein interactions observed in yeast. Human UBC was expressed as a glutathione S-transferase fusion protein (GST-human UBC) in E.coli and coupled to a glutathione matrix. (Example 4). As shown in FIG. 3A, when extracts from 293 cells transfected with WT1 expression plasmids were incubated with the GST-human UBC glutathione matrix, eluates analyzed by Western blots probed with an anti-WT1 antibody demonstrated that the GST-human UBC matrix complexed with WT1, whereas the matrix of GST alone did not. In another experiment, extracts of 293 cells transfected with WT1 and a hemagglutinin (HA)-tagged human UBC (HA-human UBC) expression vector were immunoprecipitated with an anti-WT1 antibody and analyzed with anti-HA antibody in Western blots. (Example 5). As shown in FIG. 3B, HA-tagged human UBC was identified in WT1 immune complexes from 293 cells co-transfected with both human UBC and WT1 expression vectors but not in 293 cells transfected with human UBC alone.

hUBC-9 also interacts directly with the TATA-binding protein (TBP), as demonstrated by GST capture assays. A GST fusion protein having the full-length hUBC-9 amino acid sequence captured TBP and WT1 selectively over the transcriptional factor TFIIB, which was also present in the assay. (FIG. 8). Further assays demonstrated that hUBC-9 interacts with the TBP through the highly conserved C-terminal domain of the TBP. Several mutants of hTBP were constructed. (FIG. 9A). In GST capture assays, GST/hUBC-9 captured wild-type TBP as well as several of the mutant TPB's; however, deletion of the C-terminal region of TBP (amino acid residues 196–335) significantly reduced the capture efficiency, and deletion of a larger portion thereof (amino acid residues 163–335) resulted in no interactions being detectable in the assay. (FIG. 9B). Hence, hUBC-9 specifically interacts with the C-terminal domain which includes amino acids 163-335 of the TATA binding protein. Gel mobility shift assays, discussed below, further confirmed the specificity of the interaction between TBP and hUBC-9.

The hUBC-9 Enzyme has an Active Conjugating Activity hUBC-9 is an active ubiquitin conjugating enzyme, and as such, is a member of a family of ubiquitinating enzymes. Although some variation is believed to exist in the precise amino acid sequence of mammalian ubiquitin conjugating enzymes, the active cysteine residue at position 93 (boxed, FIG. 1B) is characteristic of all of the ubiquitin conjugating enzymes discovered to date, and it has been determined that the presence of the active site cysteine is important to the ubiquitin conjugating activity. This cysteine is believed to provide the enzyme with its ability to participate in thioester formation. Hence, human UBC-9, which has 56% sequence identity to yeast UBC-9 and shares the same active cysteine site, forms an integral part of the proteolytic proteosome pathway.

Figure 4A:
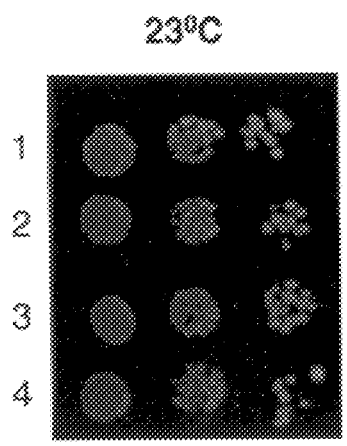
FIGS. 4A and 4B show temperature-sensitive yeast cell cultures at permissive and restrictive temperatures, respectively.
Figure 4B:
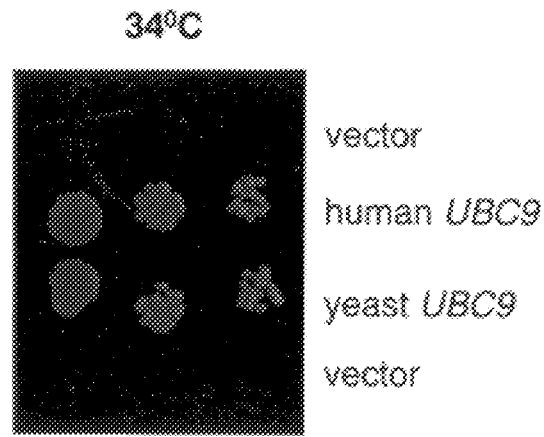

To demonstrate that the conserved cysteine residue of hUBC-9 is involved in mono-ubiquitin thioester formation, we used in vitro transcription/translation of the human UBC cDNA in the rabbit reticulocyte system, which contains the three coupled enzymes $[E_1 \ E_2 \ E_3]$ required for protein ubiquitination. Upon testing the product with 1M neutral hydroxylamine, a slower migrating protein band was detected, suggesting that human UBC contains a thioester that was hydrolyzed by hydroxylamine. In another experiment, an anti-ubiquitin antibody recognized the slower migrating band that was sensitive to hydroxylamine in Western blots. In a further experiment, we expressed the full-length hUBC-9 cDNA in a yeast carrying a temperature sensitive mutant form of yUBC-9. (Example 6). As shown in FIGS. 4A and 4B, growth was fully restored to the temperature sensitive (ts) yUBC-9 yeast at the otherwise nonpermissive temperature. The results of these experiments independently and cumulatively establish that the hUBC-9 cDNA encodes an active ubiquitin conjugating enzyme.

The Conjugating Activity of hUBC-9 Regulates Transcription

The human ubiquitin conjugating protein of the present invention is a member of a family of enzymes which, via their conjugating activity, function to regulate the cell cycle and duplication of DNA. It has now been determined, moreover, that the ubiquitin-dependent protease degradation system is directly involved in transcriptional regulation. The conjugating activity of hUBC-9 appears to modulate gene transcription by contributing to the degradation of repressor proteins such as WT1, thereby regulating the level of repressor activity.

WT1 was shown to be rapidly degraded by the ubiquitin proteosome proteolysis pathway when expressed in rabbit reticulocyte lysates containing the enzymes required for transiting the proteolysis pathway. In a control experiment, cDNA of WT1 was added to rabbit reticulocyte lysates that contained E1, E2 and E3 enzymes, ubiquitin and the 26S proteosome complex required for protein ubiquitination and degradation. A distinct band that migrated identically to WT1 was observed upon analysis in SDS gels. In an experiment in which cDNAs of both WT1 and hUBC-9 were added to the rabbit reticulocyte system, one protein band had a greatly diminished intensity relative to the band observed in the control experiment. Moreover, lower molecular weight immunoreactive species were found and a single, higher apparent molecular weight species was observed which migrated consistent with monoubiquitin-WT1. These results further confirm the interaction between hUBC-9 and WT1, and significantly, demonstrate that WT1 is degraded in a hUBC-9-dependent manner.

Figure 10A:
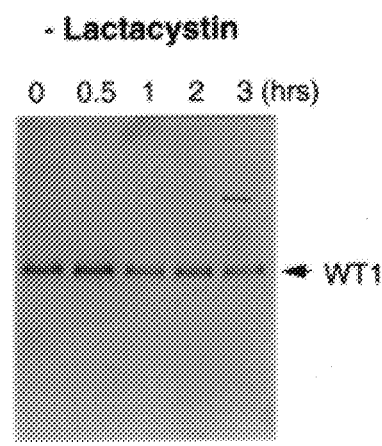
FIGS. 10A–10D show the results of WT1 turnover experiments done when WT1 is expressed by itself (FIG. 10A), when WT1 is co-expressed with hUBC-9 (FIG. 10B), when WT1 is expressed in the presence of lactocysteine, a known inhibitor of the proteolytic degradation system (FIG. 10C) and when WT1 is co-expressed with mUBC-9, a $C^{93}S$ mutant of hUBC-9 (FIG. 10D).
Figure 10B:
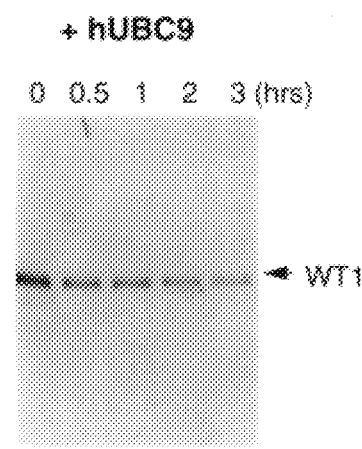
Figure 10C:
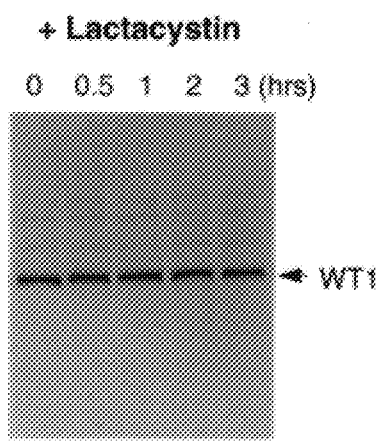
Figure 10D:
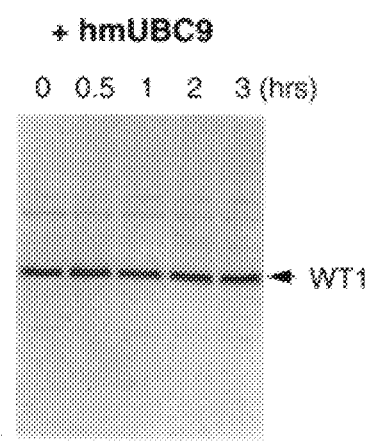

The effect of the conjugating activity is also demonstrated by inhibition of the proteolytic pathway with lactocysteine, a specific inhibitor of protease activity associated with the 26S proteosome complex, with such inhibition causing the half-life of WT1 to increase. The turnover of WT1 was tested in a series of experiments in which WT1 was (a) expressed in 293 cells alone, (b) co-expressed with hUBC-9, (c) expressed in the presence of lactocysteine, a known inhibitor of the proteolytic degradation system or (d) co-expressed with mUBC-9, a $C^{93}S$ mutant of hUBC-9. In each case, the cells were treated with cycloheximide, a protein synthesis inhibitor. Cells harvested at different times were lysed and analyzed by Western blots with anti-WT1 antibody. In the control experiment (WT1 alone), the steady state levels of WT1 decreased dramatically upon the addition of the cycloheximide and the half-life of WT1 was determined to be about 1½ hours. (FIG. 10A). The half-life of WT1 decreased when co-expressed with hUBC-9. (FIG. 10B). However, co-treatment of the cells with lactocysteine resulted in a rise in the steady state levels of WT1 by a factor of about 5. (FIG. 10C). Moreover, a similar increase in the amount of WT1 was observed when a WT1 was co-expressed with a mutant hUBC-9 which lacked ubiquitin conjugating activity due to substitution of serine at the active site cysteine. (FIG. 10D).

WT1-dependent transcriptional repression is influenced by the proteosome degradation system. When WT1 was expressed in 293 cells co-transfected with a reporter plasmid and cultured with lactocysteine (50 $\mu$M), a two-fold to three-fold enhancement of repressor activity was observed. Furthermore, the enhancement effect of lactocysteine progressively decreased as the level of expression of WT1 was increased. Lactocysteine was without effect at an upper limiting level of WT1. The conjugating activity of hUBC-9 and its effect on repression is independently demonstrated by removal of the conjugating activity. In a cotransfection experiment detailed below, it was shown that removal of the ubiquitin conjugating activity by mutation of yUBC-9 at the active cysteine site results in a greater degree of repression activity than yUBC-9 having the active site cysteine. (Example 9).

These experiments demonstrate, individually and cumulatively, that hUBC-9 has conjugating activity which is specific to the WT1 and possibly to other suppressor proteins. The conjugating activity of hUBC-9 positively influences transcription through degradation of repressors such as WT1, and possibly, of hUBC-9 itself.

UBC's have a Repressor Activity which Suppresses Transcription

Ubiquitin conjugating enzymes such as hUBC-9 and yUBC-9 have a transcriptional repression activity. The repression activity of hUBC-9 enhances the existing repressor activity of WT1 and perhaps other repressor gene products. Moreover, the suppression of gene transcription by human and yeast UBC's themselves becomes significant when these enzymes are fused to or associate via protein-protein interactions with proteins having a DNA binding domain, such as Gal4 or WT1.

Figure 5A:
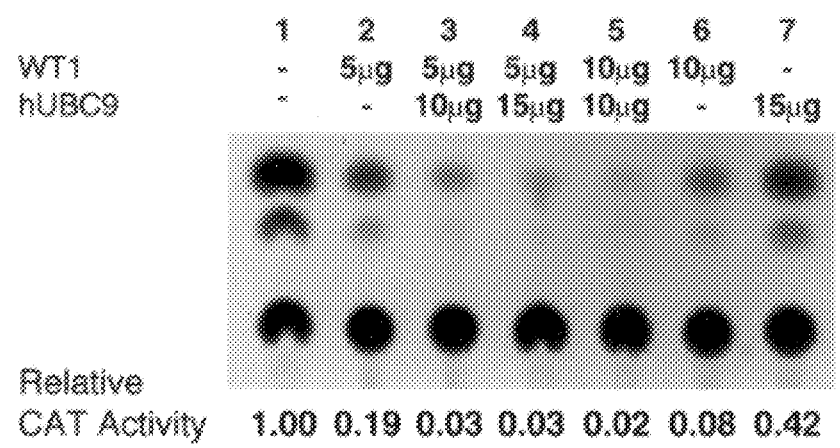
FIGS. 5A and 5B show how hUBC-9 enhances the transcriptional repressor activity of WT1 in human embryonic kidney cells (293).
Figure 5B:
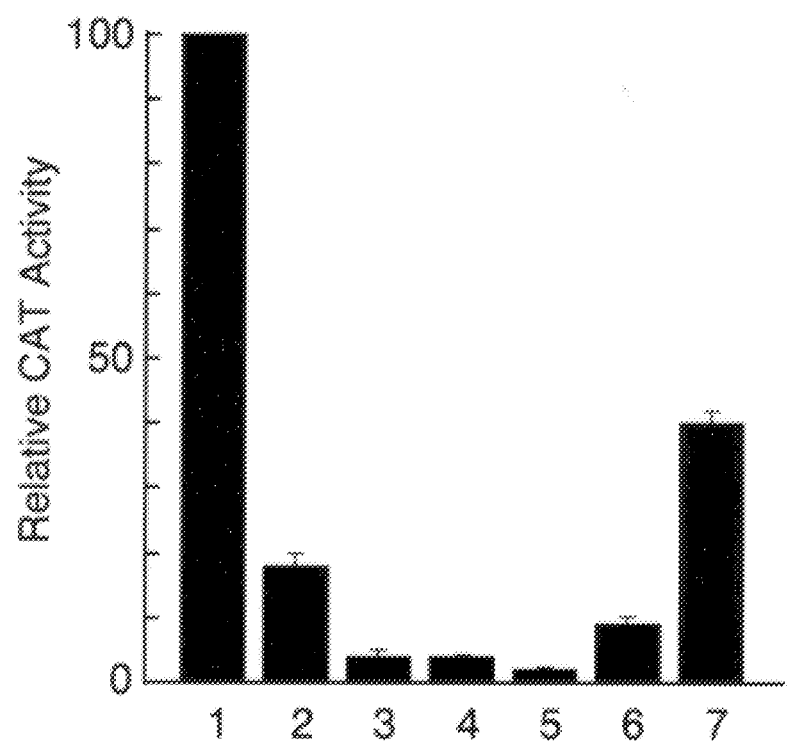

The repression activity of hUBC-9 enzyme strikingly enhances the repressor activity of Wilm's tumor suppressor gene product, WT1. The ability of human UBC to modulate the transcriptional regulatory activity of WT1 was analyzed in cotransfection experiments (Example 7). As shown in FIG. 5A, when human UBC was expressed alone at 15 $\mu$g, without WT1 and without being fused to a DNA binding domain, expression of the reporter gene was reduced slightly more than 2-fold (42% relative activity). When WT1 was expressed alone at 10 $\mu$g, expression of the reporter gene was reduced by about a factor of ten (8% relative activity). However, when human UBC was expressed together with WT1, the repressor activity of WT1 was increased by an additional four-fold factor, resulting in a total transcriptional repression of about 50-fold (2% relative activity). In additional experiments, essentially identical results were obtained (FIG. 5B). Human UBC significantly enhances the repressor activity of WT1 in vivo when both are expressed at high levels together.

Furthermore, hUBC-9 is itself a potent transcriptional repressor when it is coupled to a functional DNA binding domain recognized by an appropriate promoter element. Human UBC was coupled to the Gal4 DNA binding domain and tested with a promoter containing five upstream Gal4 DNA binding sequences (5×UAS) in co-transfection experiments. (Example 8). As shown in FIG. 6B, when human UBC was tested with the control promoter (lacking 5×UAS) reporter plasmid to which human UBC was unable to bind, the influence of human UBC was minimal (66% relative activity). However, human UBC was a powerful transcriptional repressor when it was able to directly bind, via the Gal4 binding domain, to the promoter/reporter construct containing the Gal4 DNA binding sequences. In this case, human UBC repressed promoter activity by about eight-fold (12% relative activity), establishing that human UBC alone is an effective repressor when it binds to an appropriate promoter element. When the above experiment was repeated (Example 9), the h-UBC-9/Gal4 fusion protein again demonstrated significant repression activity (15% relative activity), as shown in FIG. 7B.

These results strongly support the conclusion that human UBC has transcriptional repressor activity. The repressor activity of hUBC is particularly significant when hUBC is positioned near the promoter regions, either through protein-protein interactions with other proteins, such as WT1, or through fusion with DNA binding domains, such as Gal4, both of which appear to tether human UBC to gene-specific promoter sites.

Other ubiquitin conjugating enzymes, such as yUBC-9, also function efficiently as transcription repressors when fused to a DNA binding domain. Yeast UBC-9 was coupled to the Gal4 DNA binding domain and co-expressed with a reporter vector having five upstream Gal4 DNA binding sequences. (Example 9). As shown in FIG. 7C, when co-expressed by itself at 20 $\mu$g, the yUBC-9/Gal4 fusion protein repressed transcription by about three-fold (0.35 relative activity).

The transcriptional repression activity of UBC's is independent of their conjugating activity As noted above, UBC's have, in addition to their ubiquitin conjugating activity, a transcriptional repression activity. Significantly, the repression activity is independent of the conjugating activity, as demonstrated by data showing that yUBC-9-m, a yUBC-9 $C^{93}S$ mutant which lacks ubiquitin conjugating activity, functions efficiently as transcription repressor when fused to a DNA binding domain. Briefly, a mutant form of yUBC-9 lacking the active site cysteine at position 93 (designated yUBC-9-m), was coupled to the Gal4 DNA binding domain and co-expressed with a reporter vector having five upstream Gal4 DNA binding sequences. (Example 9). As shown in FIG. 7C, when co-expressed by itself at 20 μg, the yUBC-9-m/Gal4 fusion protein repressed transcription by about five-fold (20% relative activity).

Moreover, the independence of UBC repression activity is supported by data showing a higher degree of transcriptional repression for mutant yUBC-9-m than for yUBC-9. Referring to FIG. 7C, whereas yUBC-9 expressed alone showed a 35% relative activity, yUBC-9-m expressed alone showed a 20% relative activity—an increase in repression activity of about 15%. Consistently, when both normal yUBC-9 and mutant yUBC-9-m were co-expressed with the reporter vector in equal (10 μg) amounts, the degree of transcriptional repression was intermediate (28% relative activity) between the values for the normal or mutant strain alone.

While not being bound by theory, because the yUBC-9-m lacking the active site cysteine was active as a repressor, and further, even more active than the normal yUBC-9 having an active site cysteine, the ubiquitin conjugating activity does not appear to be required for the transcription repressor activity. Nonetheless, as discussed above, the conjugating activity of UBC-9 appears to affect and regulate the level of repressor activity. The conjugating activity of hUBC-9 facilitates proteolytic degradation of WT1 and thereby at least partially relieves the repressor effect of WT1.

hUBC-9 Functions as a Repressor Through its Interactions with the TATA Binding Protein (TBP)

Figure 11A:
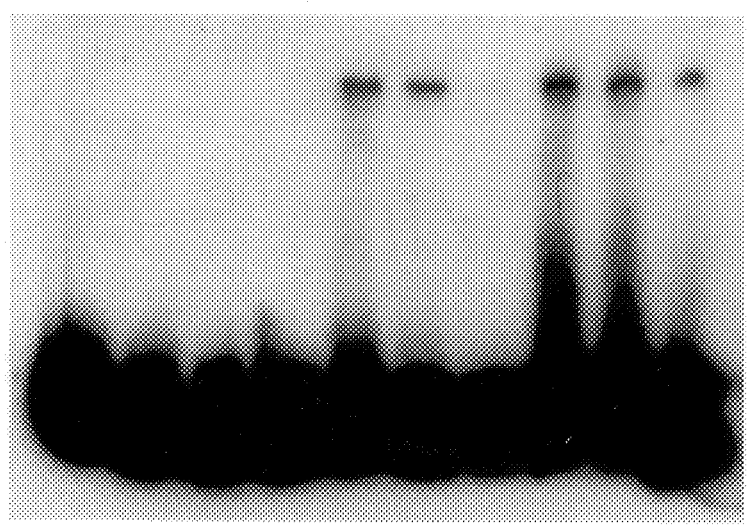
FIGS. 11A and 11B relate to gel mobility shift assays that show the interaction between hUBC-9 and the TATA binding protein (TBP).
Figure 11B:
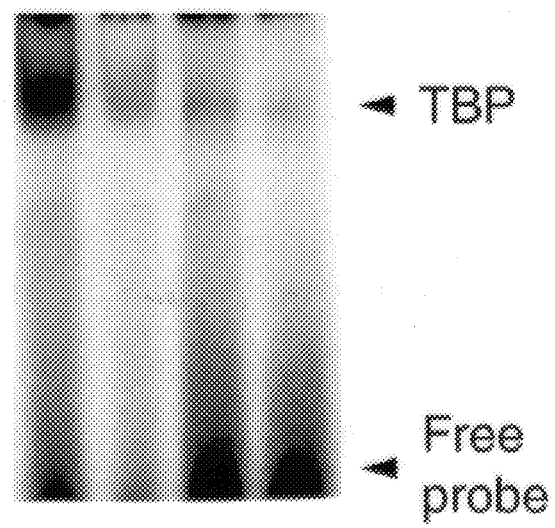

As noted, hUBC-9 interacts with the C-terminal domain of the TATA binding protein (TBP) in GST capture assays. Gel mobility shift assays confirmed this interaction, and further demonstrated that hUBC-9 appears to suppress transcription by disrupting the binding of TBP to DNA and by disrupting the formation of the transcription initiation complex. This model is consistent with the understanding that the C-terminal of TBP, with which hUBC-9 was shown to interact, contains a "face" which contacts the major groove of DNA. In the assays carried out, an end-labeled DNA probe containing the TATA box was provided an opportunity to complex with various combinations of TBP, TFIIB and hUBC-9. In control experiments in which there was no TBP present, no detectable complex was formed between hUBC-9 and the DNA probe, between TFIIB and the probe, or between hUBC-9, TFIIB and the probe. (FIG. 11A, columns A1, A2 and A3, respectively). In further control experiments, the combination of purified TBP and the DNA probe containing the TATA box resulted in a single readily detectable complex. (FIG. 11A, column B1). The addition of TFIIB strengthened the intensity of the band, as expected based on the reported ability of TFIIB to enhance the binding of TBP to the TATA sequence. (FIG. 11A, column C1). However, when the above assays were repeated using purified hUBC-9 (10 ng, 50 ng) in the systems, hUBC-9 reduced the level of complex formation between TBP and DNA (FIG. 11A, columns B2 and B3), and in subsequent experiments, between TBP and DNA in the presence of TFIIB (FIG. 11A, columns C2 and C3). Hence, hUBC-9 destabilizes TBP/DNA binding. The effect of hUBC-9 on the DNA binding ability of TBP was concentration dependent. (FIG. 11B).

Figure 12A:
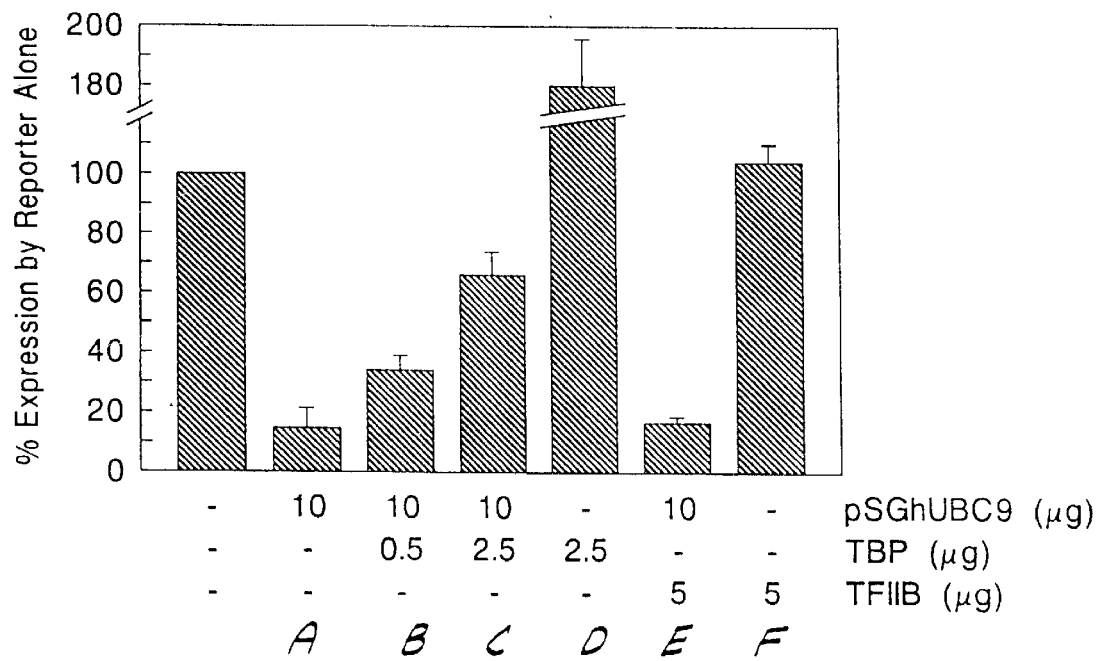
FIGS. 12A and 12B show the results of transient co-transfection assays using a 5×UAS pSV CAT reporter vector.
Figure 12B:
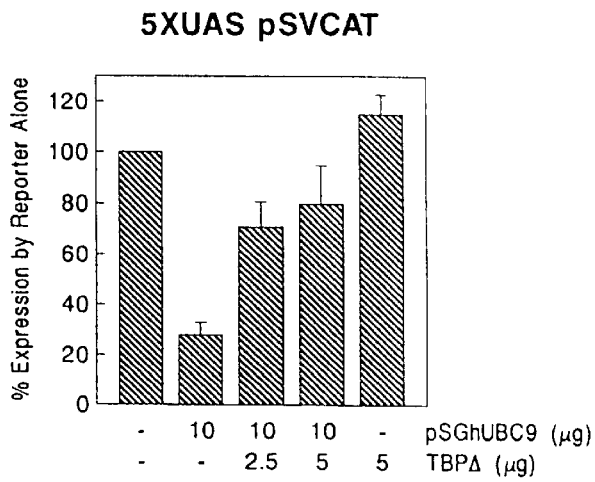

To further confirm that hUBC-9 interacts in the region of the TBP DNA binding domain, co-transfection assays were performed which demonstrated that high levels of exogenous TBP overcame the repressor activity of hUBC-9. A 5×UAS pSV CAT reporter vector was used in transient assays in which a GAL4/hUBC-9 fusion protein (pSGhUBC-9) (0 or 10 μg), TBP (0, 0.5 or 2.5 μg) and/or TFIIB (5 μg) were co-expressed in 293 cells in varying combinations. The repressor activity of hUBC-9 was significantly reduced in a concentration-dependent manner by the presence of TBP (without TFIIB). (FIG. 12A, columns A, B, C and D). The presence of TFIIB in the assay had no effect on hUBC-9 repression (FIG. 12A, columns E and F). Further experiments were performed to ensure that the observed decrease in repressor activity of hUBC-9 was not, in fact, related to an intrinsic activation of transcription due to expression of TBP. A mutant TBP was constructed which had an amino acid sequence which included the TBP domain which interacted with hUBC-9 in GST capture assays, but which did not include the amino acid residues 1-138. The mutant TPB (0, 2,5 and 5 μg), referred to herein as TBPΔ1-138, and the hUBC-9/Gal4 fusion protein (0, 10 μg) were co-expressed in various combinations in transient co-transfection assays similar to those immediately aforementioned. TBPΔ1-138 lacked the ability to substantially activate the promoter, but effectively relieved the repressor activity of hUBC-9, although to a lesser extent than wild-type TBP. (FIG. 12B). Hence, hUBC-9 is shown to interact with TBP to repress transcription. Moreover, the addition of TBP can effectively titrate hUBC-9 to relieve its repressor activity, and in effect, enhance transcription.

Figure 13:
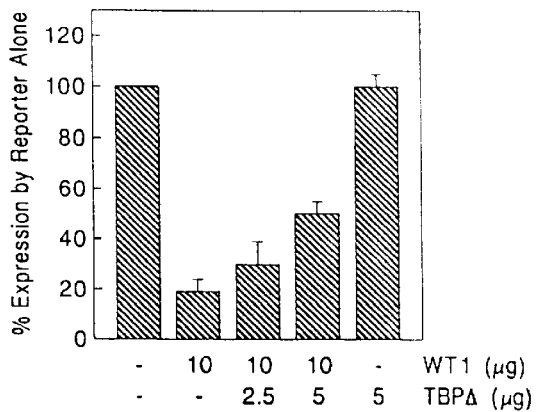
FIG. 13 shows the results of transient co-transfection assays using a 5×UAS pSV CAT reporter vector where TBPΔ1-138 (0, 2.5 and 5 μg) was co-expressed with WT1 (10 μg) in various combinations.

In similar co-transfection assays, mutant TBP, TBPΔ1-138 effectively relieved the repressor activity of WT1. (FIG. 13). Cumulatively, these results suggest that WT1 effects suppression in combination with hUBC-9 by positioning hUBC-9 through protein-protein interactions for direct hUBC-9 interaction with the TBP subunit of the TFIID transcription factor, thereby destabilizing the TBP/TATA sequence interaction, and more generally, disrupting formation of the transcription initiation complex.

Producing hUBC-9

The nucleotide sequence encoding the mammalian or yeast or other UBC enzyme, or active portion thereof, is cloned into an expression vector using known procedures. Briefly, specific nucleotide sequences in the vector are cleaved by site-specific restriction enzymes such as NcoI and HindIII. Then, after optional alkaline phosphatase treatment of the vector, the vector and a target fragment comprising the nucleotide sequence of interest are ligated together with the resulting insertion of the target codons in place adjacent to desired control and expression sequences. The particular vector employed will depend in part on the type of host cell chosen for use in gene expression. Typically, a host-compatible plasmid will be used containing genes for markers such as ampicillin or tetracycline resistance, and also containing suitable promoter and terminator sequences. A preferred plasmid into which the recombinant DNA expression sequence of the present invention may been ligated is plasmid pET. A pET plasmid which expresses human UBC-9 has been deposited in GeneBank, Ascession No.'s μ66818 and μ66867.

The plasmid comprising the DNA expression sequence for the UBC enzymes of the present invention may then be expressed in a host cell. Bacteria, e.g., various strains of E. coli, and yeast, e.g., Baker's yeast, are most frequently used as host cells for expression of mammalian UBC enzymes, although techniques for using more complex cells are known. See, e.g., procedures for using plant cells described by Depicker, A., et al., 1982. E. coli host strain X7029, wild-type F⁻, having deletion X74 covering the lac operon is utilized in a preferred embodiment of the present invention. A host cell is transformed using a protocol designed specifically for the particular host cell. For *E. coli*, a calcium treatment produces the transformation. (Cohen, S. N., 1972). Alternatively and more efficiently, electroporation of salt-free *E. coli* is performed according to the method of Dower et al., 1988. After transformation, the transformed hosts are selected from other bacteria based on characteristics acquired from the expression vector, such as ampicillin resistance, and then the transformed colonies of bacteria are further screened for the ability to give rise to high levels of isopropylthiogalactoside (IPTG)-induced thermostable DNA polymerase activity. Colonies of transformed *E. coli* are then grown in large quantity and expression of mammalian UBC enzyme is induced for isolation and purification. Example 4 details the expression of human UBC in bacteria as a GST-fusion protein. Example 6 details the expression of a temperature-sensitive yeast UBC strain in yeast.

Although a variety of purification techniques are known, all involve the steps of disruption of the *E. coli* cells, inactivation and removal of native proteins and precipitation of nucleic acids. The enzyme is separated by taking advantage of such characteristics as its weight (centrifugation), size (dialysis, gel-filtration chromatography), or charge (ion-exchange chromatography). Generally, combinations of these techniques are employed together in the purification process. In a preferred process for purifying mammalian UBC enzyme, the *E. coli* cells are weakened using lysozyme and the cells are lysed and nearly all native proteins are denatured by heating the cell suspension rapidly to 80° C. and incubating at 80°–81° C. for 20 minutes. The suspension is then cooled and centrifuged to precipitate the denatured proteins. The supernatant (containing mammalian UBC enzyme) then undergoes a high-salt polyethylene-imine treatment to precipitate nucleic acids. Centrifugation of the extract removes the nucleic acids and mammalian UBC enzyme is concentrated by use of ammonium sulfate precipitation before chromatography, preferably on a heparin-agarose column. Preferably, the purified enzyme is at least 60% (w/w) of the protein of a preparation. Even more preferably, the protein is provided as a homogeneous preparation.

Compositions

The ubiquitin conjugating enzymes disclosed herein as having transcription repression activity (e.g. hUBC-9, yUBC-9 and y-UBC9-m), as well as other ubiquitin conjugating enzymes having such an activity, or segments thereof, may be combined with an acceptable carrier, diluent or delivery agent to form a useful composition. The composition has both pharmaceutical (ie, human) and non-pharmaceutical applications. In either case, the protein used in the composition has transcriptional repressor activity. The amino acid sequence of the protein includes at least a 12 amino acid portion of a ubiquitin conjugating protein such as a UBC-9 which has a transcription repression activity. The amino acid sequence of the protein preferably includes at least a segment of hUBC-9 or yUBC-9. An active-site mutant of a ubiquitin conjugating enzyme, such as a $cys^{93}$ mutant of hUBC-9, whereby such a mutant lacks its ubiquitin conjugating activity, or a segment thereof, can also be used as the protein. A mutant in which a serine residue replaces the cysteine residue is preferred. In an alternative method for removing the ubiquitin conjugating activity from the composition, the composition can further include a biochemical inhibitor suitable for inhibiting the active site cysteine of the ubiquitin conjugating enzyme. An exemplary suitable inhibitor in n-ethyl-maleimide. The protein in the composition may have only transcriptional repressor activity, or have such an activity as well as ubiquitin conjugating activity. In use, the composition may further comprise one or more other proteins, including for example a second protein having transcriptional repressor activity, such as WT1. The composition may also comprise other proteins having a DNA binding domain with which the ubiquitin conjugating enzyme or segment thereof interacts. Moreover, the protein used in the composition may be a fusion protein which has a amino acid sequence that includes a DNA binding domain and a transcriptional repressor domain. The repressor domain of the fusion protein preferably includes at least a 12 amino acid segment of a ubiquitin conjugating enzyme having transcriptional repressor activity. The DNA binding domain is preferably a domain which binds to or interacts with or otherwise associates with a region of a gene which is sufficiently close to the promotor region to allow the ubiquitin conjugating enzyme or segment thereof to interact with the promoter region, and particularly, with the TATA binding protein at the TATA binding site. Such domains include the amino acid sequences of the Gal4 domain, the LexA domain, and the many zinc-finger domains.

For pharmaceutical compositions, the protein is combined with a pharmaceutically acceptable carrier, diluent or gene therapy delivery agent, and a pharmaceutically active amount of the protein is used in the composition. The amount is preferably an amount that is effective to achieve modulation or regulation or suppression of gene transcription of a target gene. While smaller or larger amounts may be suitable in particular applications, the pharmaceutically active amount of the protein is preferably an amount sufficient to increase the concentration of the protein in the cell of the target gene being regulated by a factor ranging from about 1% to about 1000% relative to the amount of the protein which is endogenous to the cell. The increase in concentration more preferably ranges from about 10% to about 100%. Where the protein in the pharmaceutical composition is a segment of a ubiquitin conjugating enzyme having transcriptional repressor activity, the amount is taken relative to the endogenous amount of the ubiquitin conjugating enzyme in its natural full-sequence state. The particular dosage administered for a particular pharmaceutical application, while preferably consistent with the aforementioned amounts, will be dependent upon the age, health, and weight of the recipient, type of concurrent treatment, if any, frequency of treatment, the nature of the effect desired, and whether a localized tissue or system-wide effect is being sought. For treatment of Wilm's tumor, a tumor-inhibiting amount is to be administered. Similarly, for regulating or modulating or suppressing any particular neoplastic tissue growth, an effective amount to achieve such regulation, modulation or suppression determined by the factors outlined above, is to be applied. The amount of protein used in a non-pharmaceutical application may be in a range similar to that for pharmaceutical compositions, but may also include amounts outside this range.

The nucleic acid polymers which encode a ubiquitin conjugating enzyme such as a UBC-9 having transcriptional repressor activity, or which encode a segment thereof, can be used in a nucleic acid composition in combination with a gene therapy delivery agent. As used herein, the term gene therapy relates to operations and/or manipulations affecting both human and non-human genes, whether such operations are in-vivo or ex-vivo in nature. More specifically, the composition preferably comprises a nucleic acid polymer that encodes a protein which has transcriptional repressor activity. The transcriptional repressor protein has an amino acid sequence which includes at least a portion of the amino acid sequence of a ubiquitin conjugating enzyme having transcriptional repressor activity, with the included portion being at least about 12 amino acid residues in length. Alternatively, the nucleic acid polymer can have a nucleotide sequence complementary to the nucleic acid sequence of the immediately aforementioned nucleic acid polymer. The ubiquitin conjugating enzyme can be a UBC-9 such as hUBC-9, or a segment thereof, or a mutant thereof lacking ubiquitin conjugating activity. The composition may further comprise or be used in conjunction with a biochemical inhibitor of the ubiquitin conjugating activity of the ubiquitin conjugating enzyme. The nucleic acid polymer can also encode a fusion protein such as the aforementioned fusion protein described in connection with the above-described protein composition.

For pharmaceutical use, the nucleic acid composition comprises a pharmaceutically effective amount of the nucleic acid and a pharmaceutically acceptable gene therapy delivery means. The amount of nucleic acid required will vary depending on the type of cell, the effect being sought and on the delivery system used to introduce the nucleic acid polymer into a target cell. In general, the amount of nucleic acid polymer is preferably an amount sufficient to, upon expression in the target cell, result in an amount of protein sufficient to regulate or modulate or repress transcription of the target gene. Preferably, the amount is sufficient to increase the concentration of the protein in the cell of the target gene being regulated by a factor ranging from about 1% to about 1000% relative to the amount of the protein which is endogenous to the cell of the gene being regulated. The increase in concentration more preferably ranges from about 10% to about 100%. Where the nucleic acid polymer of the agent encodes a protein which is a segment of a ubiquitin conjugating enzyme having transcriptional repressor activity, the amount is taken relative to the endogenous amount of the ubiquitin conjugating enzyme in its natural full-sequence state.

Gene therapy delivery agents are used to introduce the nucleic acid polymer into target cells or to enhance the uptake of the nucleic acid polymer by the target cells. Several approaches for introducing the nucleic acid polymer into the cell and effecting expression thereof are known and practiced by those of skill in the art. (Mulligan, R., *The Basic Science of Gene Therapy*, SCIENCE, Vol. 260, pp.926–32 (1993)). In one approach, the nucleic acid polymer of the composition may be combined, complexed, coupled or fused with a delivery agent which introduces the nucleic acid polymer into a human cell in vivo. For example, the nucleic acid may be combined with a lipophilic cationic compound, which may be in the form of liposomes. The use of liposomes to introduce genes or other pharmaceutically active ingredients into cells is taught, for example, in U.S. Pat. Nos. 4,397,355 and 4,394,448. Alternatively, said nucleic acid may be combined with a lipophilic carrier such as any one of a number of sterols including cholesterol, cholate and deoxycholic acid. A preferred sterol is cholesterol. Additionally, the nucleic acid may be conjugated to a peptide that is ingested by cells. Examples of useful peptides include peptide hormones or antibodies. By choosing a peptide that is selectively taken up by Wilm's tumor or other neoplastic cells, specific delivery of the nucleic acid may be effected. The nucleic acid may be covalently bound to the peptide via methods well known in the art. The peptide of choice may then be attached to the activated enzyme via an amino and sulfydryl reactive hetero bifunctional reagent. The latter is bound to a cysteine residue present in the peptide. Upon exposure of target cells to the nucleic acid bound to the peptide, the nucleic acid is endocytosed and is rendered available for modulation of gene transcription. The nucleic acid polymer of the present invention can also be delivered to specific tissues using a DNA-antibody conjugate, such as is described in U.S. Pat. No. 5,428,132 to Hirsch et al. Other gene therapy delivery agents used to introduce sense or antisense nucleic acid polymers such as DNA and RNA into human cells are disclosed in U.S. Pat. Nos. 5,460,831 to Gelman et al. and 5,433,946 to Allen et al.

In an alternative approach, the gene therapy delivery agent is a construct having cDNA which includes the nucleic acid polymer and which can be expressed in a host cell. Such a construct is infected or transfected into the cell and expresses the ubiquitin conjugating enzyme having transcriptional repressor activity in the cell. For example, the composition can be a virus having a viral genome which comprises the nucleic acid polymer of the agent or which is complexed to the nucleic acid polymer of the agent. Such methods are taught, for example, in U.S. Pat. Nos. 5,252,479 to Srivastava, 5,521,291 and 5,547,932 to Birnstiel et al., 5,512,421 to Burns et al., 5,240,846 to Collins et al., 5,112,767 to Roy-Burman et al. and 5,543,328 to McClelland et al.

In yet another approach, the gene therapy delivery agent is a human cell. The nucleic acid polymer of the composition is inserted into a human cell in vitro and the cell comprising the nucleic acid polymer is then introduced into the body. The encoded ubiquitin conjugating enzyme is then expressed by the cells in vivo. Such a method is taught for example, in U.S. Pat. No. 5,399,346 to Anderson et al.

The composition comprising the nucleic acid polymer and the pharmaceutical compositions comprising the protein of the present invention may be administered by any means that achieve their intended purpose. For example, administration may be by parenteral, subcutaneous, intravenous, intramuscular, intraperitoneal, or transdermal routes. Formulations for parenteral administration can include aqueous solutions of the composition or pharmaceutical composition in water-soluble form, for example, water-soluble salts. In addition, suspensions of the active compounds in oily injection suspensions may be administered. Suitable lipophilic solvents or vehicles include fatty oils, for example, sesame oil, or synthetic fatty acid esters, for example, sodium carboxymethyl cellulose, sorbitol, and/or dextran. Optionally, the suspension may also contain stabilizers. The particular gene therapy delivery agent used in the composition of the present invention and the determination of optimal ranges of effective amounts of each component is within capacities of a person of skill in the art of the art.

The pharmaceutical compositions of the present invention can be used in a variety of pharmaceutical and non-pharmaceutical applications. In general, gene transcription in cells can be regulated, enhanced or repressed, by controlling the concentration of UBC-9 and/or of TBP to which a target gene is exposed or in which a target gene comes in contact. In particular, repression of transcription can be carried out in a gene-specific manner by positioning the UBC enzymes near the promoter regions of various genes, for example, by fusion of a UBC-9 repressor domain with a gene-specific DNA binding domain, or alternatively, by protein-protein interactions between UBC-9 and proteins associated with the promoter region or involved with transcription initiation, such as WT1, TBP, or others.

A variety of cells can be used in the present invention. Eukaryotic cells are particularly preferred, as naturally occurring eukaryotic cells contain genes having promoter regions which include a TATA box. hUBC-9 or other UBC-9's or other ubiquitin conjugating enzymes having transcriptional repressor activity or segments thereof which are at least about 12 amino acid residues in length can disrupt the TATA binding protein's role in transcription initiation in such genes. For example, the cells can be fungal cells (e.g. yeast cells), plant cells, non-human animal cells, non-human mammalian cells and human cells. Non-eukaryotic cells such as *E. Coli* can also be used where the cells comprise genetically engineered nucleic acid polymer constructs which include a promoter region which involves TBP for initiation of transcription.

The function of repressor gene products such as WT1 can be strikingly enhanced by such an approach, allowing for control of transcription of genes promoters on which WT1 is known to operate, such as IGF-II, PDGF A-chain, CSF-1 and IGF-R or others later discovered. The regulation of transcription can also be controlled by localized inhibition of the conjugating activity of UBC-9, for example, through a $^{93}$cys mutant enzyme lacking such activity, or through agents which inhibit the active cite cysteine or which otherwise interrupt the proteolytic degradation pathway in a specific manner. The regulation of transcription is particularly useful in medical treatment, diagnostic and research applications. For example, UBC-9 can be used in therapeutic compositions for inhibiting neoplastic tissue growth by itself, or in combination with known tumor suppressor proteins such as WT1. It is particularly suited to treating Wilm's tumors and to treating the other types of tumors with which WT1 suppressor gene is associated, including for example leukemia and mesothelioma. It can also be useful in controlling any number of human diseases which are causally linked to an overabundance of a certain protein. The gene from which the overabundant protein is expressed could be exposed to a UBC-9 or other ubiquitin conjugating enzymes which have repressor activity to decrease the amount of overabundant protein expressed. In certain circumstances, the repressor activity of a UBC-9 or of other ubiquitin conjugating enzymes could be applied to effect an increase in the expression of a particular protein of interest. An increase in a protein of interest can be effected through a "rebound" mechanism, where the increase therein is a result of a natural biochemical mechanism following a decrease in the amount of a second protein present in the system. The decrease in the amount of the second protein is accomplished according to the methods of the present invention directed to the gene which encodes that protein. Another significant application of the present invention includes the treatment of a human viral infection. This application would include exposing the viral genome of human virus, and particularly, the promoter region of the genome, to a ubiquitin conjugating enzyme having transcriptional repressor activity. By suppressing transcription of a viral genome, the virus may be killed or at least controlled. The invention could also be used to kill or at least help control yeast infections.

Moreover, transcription regulation is useful in a variety of non-human, non-pharmaceutical applications. The invention could, for example, be used for the treatment of animals or of particular animal diseases much as described above. The present invention is also useful for treating plant diseases resulting from overabundant expression, and may have other plant applications as well.

In another set of non-therapeutic applications, hUBC-9 may be used to develop animal-based models or in-vitro assays. For example, an animal having a selective protein deficiency can be developed by administering the pharmaceutical composition or the biochemical agent of the present invention to an animal whereby transcription of a target gene encoding the protein of interest is repressed by the repressor activity of a UBC-9 or other ubiquitin conjugating enzyme having a repressor activity. An alternative application could include an in-vitro comparative assay in which the effect of hUBC-9 on a culture of neoplastic cells or other cells of interest (e.g. 293 cells) is used as a standard against which the effect of other potential anti-cancer agents could be evaluated.

Enzymatic conversion processes, in which chemicals are commercially produced using enzymes expressed in cells can also take advantage of the present invention. Exemplary bioconversion processes include the yeast-catalyzed processes associated with the brewing and baking industries, and as well as the commercial production of a variety of carboxylic acids, including essential amino acids or analogs thereof, from amides or nitriles. The invention can also be used in bioconversion processes which are integral to bioremediation measures being carried out to effect environmental cleanup. The cells used in such enzymatic conversion processes can be eukaryotic cells or non-eukaryotic cells, such as genetically engineered *E. coli* cells. Other uses and applications of the several aspects of the invention will be apparent to those skilled in the art.

The following examples illustrate the principles and advantages of the invention.

EXAMPLES

All molecular biological manipulations used in carrying out the experiments upon which the following examples are based were performed using methods known in the art, as described, for example, in Sambrook et al., *Molecular Cloning, A Laboratory Manual*, Cold Springs Harbor Laboratory Press, Cold Springs Harbor, N.Y. (1989).

Example 1

Isolation of hUBC-9

The repressor domain (residues 85-179) within the N-terminal region of each of the alternative splice variants of WT1 were previously mapped and identified as functioning independently as a potent repressor when fused to a Gal4 binding domain. (Wang, Z.-Y., et al. 1993). This repressor domain was also shown to block the repressor function of WT1 if expressed independently without a functional DNA binding domain, suggesting that the repressor domain lacking DNA binding activity competed with WT1 for an interactive nuclear factor needed for WT1 to function as transcription repressor. (Wang, Z.-Y., et al., 1995).

The interactive factor, now identified as hUBC-9, was isolated by using a yeast two hybrid screen. A vector, LexADB-WT-N, was constructed by coupling residues 85-179 of human WT1 with the Lex DNA binding domain. To construct pLexADB/WT-N, a cDNA fragment encoding the negative regulating domain (residues 85-179) of WT1 was obtained by digestion of the plasmid PSGWT-N with XbaI, blunt ended with Klenow fragment and the EcoRI digestion, and cloned into EcoRI and SmaI treated vector pStop116, which was modified from plasmid pBTM116 by introducing stop codons in each of three reading frames within the polylinker region.

The vector expressed a fusion protein with the LexA DNA binding (DB) domain and the negative regulatory domain of WT1 (WTN) as "bait". Yeast strain L40 was used in library screening. L40 was transformed with pLexADB/WT-N and then with the Gal4 activation domain fused with human placenta cDNA library (Clontech, Calif.) as recommended by the manufacturer. Two million yeast transformants were screened. Positive colonies on His⁻ plates were further tested for β-Galactosidase activity with a filter assay. Positive clones were tested for specificity with a LexADB/lamin C hybrid, LexADB/WT-INS (containing residues 250-266 of WT1), LexADB/WT-N, and the LexADB vector alone. Plasmids reactive only with plexADB/WT-N were recovered from yeast and used to transform HB101 via electroporation and selected on leu⁻, amp⁺ minimal media. 65 positive clones were identified in the initial screening.

The 65 positive plasmids recovered were re-introduced to yeast to re-check specificity and for quantitation of β-gal activity. β-galactosidase activity units are shown, in Table 2, for the DNA-binding domain fusion partner coupled with the vector alone and with the vector fused with hUBC-9 fused with the Gal4 activation domain. Table 2 shows the binding specificity of hUBC-9 to the negative regulatory domain of WT1 in the yeast two hybrid system.

TABLE 2

Binding Specificity of hUBC-9 in Two-Hybrid System

| DNA-binding domain fusion partner | *-Galactosidase activity | |
|---|---|---|
| | Vector | hUBC-9 |
| Vector alone: | N.D. | 0.2 ± 0.1 |
| + WT 85–179: | 0.3 ± 0.2 | 57.9 ± 16.2 |
| + WT 250–266: | 0.2 ± 0.2 | 0.3 ± 0.2 |
| + Lamin C: | 0.3 ± 0.1 | 1.5 ± 0.5 |

Eleven positive clones which remained specific to WT1 were sequenced using dideoxy NTPs and sequenase 2.0 according to the manufacturer's specifications (U.S. Biochemical). Sequence analysis and homology searches were performed using GCG program (GCG, Madison, Wis.). Each of the inserts was in the same reading frame as the Gal4 activation domain. Seven of these plasmids encoded the same protein that we designated human UBC. The insert of the longest cDNA clone detected transcripts of approximately 2.8 and 1.3 kb in Northern blot analysis.

To seek full-length cDNAs, we rescreened a human placenta cDNA library with probes obtained with the two hybrid screen and isolated eight independent clones after tertiary screening. Five clones contained a 1.1 kb DNA fragment, one contained a 1.8 kb DNA fragment and two clones contained small DNA fragments that were not further analyzed. The 1.8 kb cDNA and 1.1 kb cDNA were fully sequenced. The two clones share the same sequences within the coding region and 3' end but alternative splicing appears to introduce a long 5' untranslated region (5' UTR) upstream of the translation initiation site of the longer cDNA isoform. Multiple start and stop codons were identified in all three reading frames within the long 5' UTR, indicating that the protein product of the longer transcript may be under strict translational regulation. In vitro transcription/translation of both mRNAs produced the same size protein but the longer cDNA clone expressed less than 20% of the protein product than was expressed from the shorter mRNA (data not shown), confirming that the long 5' UTR sharply reduces translation efficiency. Because the 5' UTR of the long form contains multiple intervening start and stop codons in all three reading frames (FIG. 1A), it seems likely that the presence of these codons may negatively regulate the rate of translation in the longer mRNA isoform.

In control experiments, LexADB-WT-N failed to activate transcription of reporter genes containing LexA binding sites in yeast when analyzed alone.

Example 2
Northern Blot Analysis of Human Tissues

A human tissue Northern blot (Clontech, Calif.) was probed with 1.1 kb hUBC-9 cDNA, according to the manufacturer's recommendation. FIG. 2A shows the Northern blots of hUBC-9 in different human tissues. Each lane contained 2 μg poly A⁺ RNA from heart (H), brain (B), placenta (Pl), lung (Li), smooth muscle (SM), kidney (K), pancreas (Pa). The β-actin cDNA was used to probe the same blot as control. The size markers are indicated on the left side of the blot.

Example 3
Analysis of Human Genomic DNA for hUBC-9 Gene

Figure 2B:
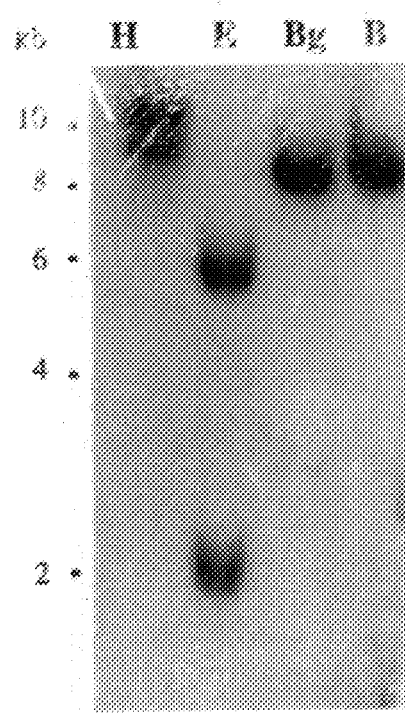

10 μg of human genomic DNA (Promega, Madison Wis.) were digested with Hind III (H), EcoRI (E), Bg1 II (Bg), or BamHI (B). The digested DNA was separated by electrophoresis on 1% agarose gel and Southern blot was performed with the full-length 1.1 kb hUBC-9 cDNA as probe. FIG. 2B shows the Southern blot analysis of the hUBC-9 gene.

Example 4
Expression of GST-hUBC-9 Fusion Protein in E. coli

Briefly, hUBC-9 was fused with glutathione S-transferase (GST) by expression in bacteria as a GST-hUBC-9 fusion protein. GST-hUBC-9 and GST were independently coupled to a reduced glutathione sepharose matrix and washed extensively. Extracts from 293 cells which had been transfected with vectors expressing WT1 and various WT1 domains were then passed over the columns, and after incubating and washing, eluates were obtained. The eluates were separated by SDS-PAGE, transferred to nitrocellulose filter for immunoblotting, and analyzed by Western blot using anti-WT1 (1:500) and anti-IgG coupled with peroxidase. The blot was visualized by color fluorography.

To construct GST-hUBC-9, pBS-hUBC-9 was digested with EcoRI and the 1.1-kb insert was subcloned into the EcoR1 site of the PGEX-KG vector containing GST in frame. E. coli strain DH5α was transformed with GST-hUBC-9 and GST-hUBC-9 was extracted and purified on glutathione-sepharose beads. GST and GST-hUBC-9 fusion protein were independently bound to glutathione-Sepharose beads and washed extensively.

WT1 and various domains thereof were expressed in 293 cells as previously described (Wang et al., 1993). Extracts were made from 2×10⁶ 293 (human embryonic kidney cell) cells transfected with CMV promoter driven expression vectors encoding full length and the WT1Δ1-84, WT1Δ1-294, and WT1Δ297-429 domains of WT1.

In vitro binding assays were performed by incubating the extracts with the sepharose beads containing 2–3 μg of GST and GST-hUBC-9 in lysis buffer (50 mM Tris (pH 7.4), 150 mM NaCl, 5 mM EDTA, 0.1% NP-40, 50 mM NaF, 1 mM PMSF, 1 μg leupeptin/ml, 1 μg antipain/ml) for 2–3 hours at room temperature. Complexes were washed extensively with lysis buffer and lysis buffer with 0.5M NaCl, boiled in SDS PAGE loading buffer (1% SDS, 10% β-mercaptoethanol), and run on 5% SDS-polyacylamide gels. Gels were transferred to nitrocellulose membranes (SOSNC) and immunoblotted with polyclonal anti-WT1 antibodies SC089 and SC189 (Santa Cruz, Calif.), which recognize the N-terminal and C-terminal domains of WT1, respectively. Following the addition of an alkaline phosphatase-conjugated secondary antibody, bound WT1 protein was visualized with 5-bromo-4-chloro-3-indolyphosphate toluidinium and nitro blue tetrazolium (BCIP, NBT; Promega, Madison, Wis.).

FIG. 3A shows the in vitro binding of WT1 and hUBC-9. The left column shows the cell lysate control results with the arrow indicating WT1 at the expected estimated molecular mass of 14 kd. The right column shows the GST control results. The middle column shows the results for the GST-hUBC-9 fusion protein with the associated arrows indicating binding between WT1 and the GST-hUBC-9 matrix. Because no similar binding was observed between WT1 and the GST control matrix, these results demonstrate that WT1 binds to or associates with hUBC-9.

Example 5
Cell Cotransfection with WT1 and HA-tagged Human UBC

An expression vector encoding the influenza virus hemagglutinin (HA) tagged hUBC-9 was constructed by cloning the 1.1 kb EcoRI fragment of hUBC-9 into the EcoRI site of expression vector PGCN (REF) in frame with a cDNA fragment encoding the HA peptide.

293 cells were cotransfected with WT1 and HA-tagged hUBC-9 expression plasmids. Cellular lysates were prepared and the extracts were immunoprecipitated with either anti-WT1 antibody or a nonspecific rabbit polyclonal antibody (anti-Gal4DB). WT1 associated proteins were separated on 15% SDS-PAGE and blotted. The blot was then analyzed by probing with anti-HA monoclonal antibody which recognized the HA tagged hUBC-9.

FIG. 3B shows the results of the co-immunoprecipitation of WT1 and hUBC-9.

Example 6
Co-Expression of hUBC-9 with ts yUBC-9

Yeast strain W9432 (MATa, ubc9-Δ1::TRP1, pSE362 [ARS1, CEN4, HIS3]-ubc9-1) is isogenic to W303 except for carrying a replacement of the genomic yUBC-9 coding sequence by the TRP1 marker and a plasmid-borne copy of the temperature sensitive yUBC-9-1 allele (1.5 kb Xba1-Ssp1 fragment).

hUBC-9 cDNA (1.1 kb EcoRI fragment) and yUBC-9 gene (0.6 kb EcoRI-XbaI fragment) were each fused to the Gal1 promoter in vectors p416GAL1 (ARSH4, CEN6, URA3) and pSE936 (ARS1, CEN4, URA3), respectively.

Referring to FIGS. 4A and 4B, the temperature-sensitive yeast strain (W9432) was independently transformed with the hUBC-9 (Row 1) and yUBC-9 (Row 4) control vectors (p416GAL1 and pSE936, respectively) and with a construct expressing hUBC-9 cDNA (Row 2) or the yUBC-9 gene (Row 3). To compare growth of these strains, cells were spotted in a dilution series on galactose-containing plates and incubated for 3.5 days at the permissive temperatures (23° C.) or 2 days at the restrictive temperature (34° C.).

Example 7
hUBC-9/WT1 Co-transfection Experiments 293 cells were co-transfected by calcium phosphate/DNA precipitation with hUBC-9 and WT1 expression constructs under the control of the CMV promoter and with a PDGF A-chain promoter driven CAT reporter plasmid.

The total amount of CMV promoter sequence transfected into each dish was equalized in each transfection by the addition of vector DNA. Transfection efficiency were standardized by co-transfection of a CMV promoter driven β-galactosidase reporter construct. All experiments were repeated at least three times.

FIG. 5A shows the results of the CAT assay and β-galactosidase assays. CAT activity was quantitated by scintillation counting of excised sections of TLC plates. FIG. 5B shows the relative CAT activity values from different assays at different times, including the standard deviation of each. The experiments demonstrate that hUBC-9 enhances the transcriptional repressor activity of WT1 in human embryonic kidney cell (293 cell).

Example 8
hUBC-9-Gal4 Cotransfection Assay hUBC-9 was coupled to the Gal4 DNA binding domain and evaluated for its effect on transcription in a reporter system.

Referring to FIG. 6A, a control expression vector, pSG424, was constructed with a SV40 promoter driven Gal4 DNA binding domain. A fusion protein expression vector, pSG-hUBC-9, was constructed with full length cDNA of hUBC-9 fused with Gal4 DNA binding domain driven by SV40 promoter. pSG-hUBC-9 was constructed by inserting an EcoRl DNA fragment containing full length of hUBC-9 cDNA into the EcoRl site of expression vector pSG424. Reporter plasmids pSV CAT and 5×UAS pSV CAT were provided by Dr. S. Weintraub (Washington University at St. Louis). The pSV CAT plasmid included a SV40 promoter fused with CAT reporter gene (Promega, Madison, Wis.). The 5×UAS pSV CAT plasmid included a pSV CAT plasmid with additional 5 copies of the Gal4 binding sites upstream of the SV40 promoter.

Co-transfection experiments were done in which each of the expression vectors were cotransfected with each of the reporter plasmids. 5 μg of reporter plasmid DNA were used in each transfection with various amounts of expression plasmids. FIG. 6B shows the results of CAT and β-galactosidase assays, performed as described above (Example 7), for different amounts of expression plasmids, as indicated. CAT activity is shown as CAT activity relative to the control alone.

Example 9
hUBC-9, yUBC-9 and vUBC-9-m Gal4 Fusion Proteins hUBC-9, yUBC-9 and yUBC-9-m (a mutant yUBC-9 with serine in place of the active site cysteine) were independently coupled to a Gal4 DNA binding domain and evaluated for effect on transcription in a reporter system.

Referring to FIG. 7A, control expression vector, pSG424, and hUBC-9/Gal4 fusion protein expression vector, pSG-hUBC-9, were constructed as described above (Example 8). A yUBC-9/Gal4 expression vector, pSG-yUBC-9, was constructed by inserting an EcoRl DNA fragment containing full length of yUBC-9 cDNA into the EcoRl site of expression vector pSG424. A yUBC-9-m/Gal4 expression vector, pSG-yUBC-9-m, was constructed by digestion of pUC19-yUBC9-m plasmid with HindIII, blunted with Klenow fragment, and then digested by EcoRI and cloned into EcoRI-SmaI digested pSG424 plasmid. The reporter plasmids, depicted in FIG. 7A, were as obtained described above (Example 8).

The results of CAT and β-galactosidase assays, performed as discussed above (Example 7), for cotransfection experiments are shown in FIG. 7B and 7C for human and yeast UBC's, respectively. 5 μg of reporter plasmid DNA were used in each transfection with various amounts of expression plasmids, as indicated.

In light of the detailed description of the invention and the examples presented above, it can be appreciated that the several objects of the invention are achieved. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

BIBLIOGRAPHY

Cohen, S. N., 1972: Proc. Natl. Acad. Sci. 69:2110 (1972)

Depicker, A., et al., 1982: *J. Mol. Appl. Gen.* (1982) 1:561.

Dower et al. (1988), Nucleic Acids Research 16:6127–6145.

Goeble, M. G., et al., 1988: The yeast cell cycle gene CDC34 encodes a ubiquitin-conjugating enzyme. Science, 1988. 241 (4871): p. 1331–5

Seufert, W. et. al., 1995: Role of a ubiquitin-conjugating enzyme in degradation of S- and M-phase cyclins. Nature, 1995. 373(6509): p. 78–81.

Wang, Z.-Y., et al., 1995: WT1, the Wilms' tumor suppressor gene product, represses transcription through an interactive nuclear protein. Oncogene, 1995. 10: p. 1243–1247].

Wang, Z.-Y., et al., 1993: Identification of a single-stranded DNA-binding protein that interacts with an S1 nuclease-sensitive region in the platelet-derived growth factor A-chain gene promoter. J. Biol. Chem., 1993a 268 (No. 14, May 15), p. 9172, p. 10681–10685.

We claim:

1. A eukaryotic host cell co-transfected with a deoxyribonucleic acid polymer encoding a transcriptional repressor protein, and with a deoxyribonucleic acid polymer encoding an adapter protein, the adapter protein having transcriptional repressor activity and an amino acid sequence which includes at least a portion of the amino acid sequence of a ubiquitin conjugating enzyme having transcriptional repressor activity, the included portion being at least about 12 amino acid residues in length and conferring the repressor activity on the adapter protein.

2. The host cell of claim 1 wherein the ubiquitin conjugating enzyme has transcriptional repressor activity and a mutated active site cysteine residue, whereby the mutated enzyme lacks ubiquitin conjugating activity.

3. The host cell of claim 1 wherein the ubiquitin conjugating enzyme is UBC-9.

4. The host cell of claim 1 wherein the ubiquitin conjugating enzyme is hUBC-9 or yUBC-9.

5. The host cell of claim 1 wherein the ubiquitin conjugating enzyme is hUBC-9.

6. The host cell of claim 1 wherein the transcriptional repressor protein is WT1.

7. The host cell of claim 1 wherein the transcriptional repressor protein is WT1 and the adapter protein is UBC-9.

8. The host cell of claim 1 wherein the adapter protein is (a) a ubiquitin conjugating enzyme having transcriptional repressor activity or (b) a ubiquitin conjugating enzyme having transcriptional repressor activity and having a mutated active site cysteine residue, whereby the mutated enzyme lacks ubiquitin conjugating activity.

9. The host cell of claim 8 wherein the ubiquitin conjugating enzyme is UBC-9.

10. The host cell of claim 8 wherein the ubiquitin conjugating enzyme is hUBC-9 or yUBC-9.

11. The host cell of claim 8 wherein the ubiquitin conjugating enzyme is hUBC-9.

12. The host cell of claim 8 wherein the transcriptional repressor protein is WT1.

13. The host cell of claim 8 wherein the transcriptional repressor protein is WT1 and the adapter protein is UBC-9.

14. The host cell of claim 1 wherein the cell is transfected with a first vector comprising the deoxyribonucleic acid polymer encoding a transcriptional repressor protein, and cotransfected with a second vector comprising the deoxyribonucleic acid polymer encoding an adapter protein.

15. A eukaryotic host cell transformed with a plasmid vector comprising DNA, the DNA comprising a deoxyribonucleic acid polymer which encodes a fusion protein having transcriptional repressor activity, the fusion protein comprising a DNA binding domain and a transcriptional repressor domain, the transcriptional repressor domain having an amino acid sequence which includes at least a portion of the amino acid sequence of a ubiquitin conjugating enzyme having transcriptional repressor activity, the included portion being at least about 12 amino acid residues in length and conferring the repressor activity on the fusion protein.

16. The host cell of claim 15 wherein the transcriptional repressor domain of the fusion protein has the amino acid sequence of a UBC-9 protein.

17. The host cell of claim 15 wherein the transcriptional repressor domain of the fusion protein has the amino acid sequence of hUBC-9, SEQ ID NO: 3.

18. The host cell of claim 15 wherein the transcriptional repressor domain of the fusion protein has the amino acid sequence of yUBC-9, SEQ ID NO: 4.

19. A cell culture comprising a eukaryotic host cell of claim 1.

20. A cell culture comprising a eukaryotic host cell of claim 15.

21. A fusion protein having transcriptional repressor activity, the fusion protein comprising a DNA binding domain and a transcriptional repressor domain, the transcriptional repressor domain having an amino acid sequence which includes at least a portion of the amino acid sequence of a ubiquitin conjugating enzyme having transcriptional repressor activity, the included portion being at least about 12 amino acid residues in length and conferring the repressor activity on the fusion protein.

22. The fusion protein of claim 21 wherein the ubiquitin conjugating enzyme has transcriptional repressor activity and a mutated active site cysteine residue, whereby the mutated enzyme lacks ubiquitin conjugating activity.

23. The fusion protein of claim 21 wherein the ubiquitin conjugating enzyme is UBC-9.

24. The fusion protein of claim 21 wherein the ubiquitin conjugating enzyme is hUBC-9 or yUBC-9.

25. The fusion protein of claim 21 wherein the ubiquitin conjugating enzyme is hUBC-9.

26. The fusion protein of claim 21 wherein the amino acid sequence of the transcriptional repressor domain includes the amino acid sequence of (a) a ubiquitin conjugating enzyme having transcriptional repressor activity or (b) a ubiquitin conjugating enzyme having transcriptional repressor activity and having a mutated active site cysteine residue, whereby the mutated enzyme lacks ubiquitin conjugating activity.

27. The fusion protein of claim 26 wherein the ubiquitin conjugating enzyme is UBC-9.

28. The fusion protein of claim 26 wherein the ubiquitin conjugating enzyme is hUBC-9 or yUBC-9.

29. The fusion protein of claim 26 wherein the ubiquitin conjugating enzyme is hUBC-9.

30. The fusion protein of claim 21 wherein the DNA binding domain has an amino acid sequence which includes the amino acid sequence of a domain selected from the group consisting of Gal4, LexA or a zinc-finger domain.

31. A nucleic acid polymer encoding a fusion protein having transcriptional repressor activity, the fusion protein comprising a DNA binding domain and a transcriptional repressor domain, the transcriptional repressor domain having an amino acid sequence which includes at least a portion of the amino acid sequence of a ubiquitin conjugating enzyme having transcriptional repressor activity, the included portion being at least about 12 amino acid residues in length and conferring the repressor activity on the fusion protein.

32. A plasmid vector comprising DNA, the DNA comprising a deoxyribonucleic acid polymer which encodes a fusion protein having transcriptional repressor activity, the fusion protein comprising a DNA binding domain and a transcriptional repressor domain, the transcriptional repressor domain having an amino acid sequence which includes at least a portion of the amino acid sequence of a ubiquitin conjugating enzyme having transcriptional repressor activity, the included portion being at least about 12 amino acid residues in length and conferring the repressor activity on the fusion protein.

33. The plasmid vector of claim 32 wherein the transcriptional repressor domain of the fusion protein has the amino acid sequence of a UBC-9 protein.

34. The plasmid vector of claim 32 wherein the transcriptional repressor domain of the fusion protein has the amino acid sequence of hUBC-9, SEQ ID NO: 3.

35. The plasmid vector of claim 32 wherein the transcriptional repressor domain of the fusion protein has the amino acid sequence of yUBC-9, SEQ ID NO: 4.

36. A composition comprising
   a first protein having transcriptional repressor activity,
   a second protein having transcriptional repressor activity and having an amino acid sequence which includes at least a portion of the amino acid sequence of a ubiquitin conjugating enzyme having transcriptional repressor activity, the included portion being at least about 12 amino acid residues in length and conferring the repressor activity on the second protein, and
   a carrier, diluent or delivery agent.

37. The composition of claim 36 wherein the first protein is WT1.

38. A composition comprising a
   a fusion protein having transcriptional repressor activity, the fusion protein comprising a DNA binding domain and a transcriptional repressor domain, the transcriptional repressor domain having an amino acid sequence which includes at least a portion of the amino acid sequence of (a) a ubiquitin conjugating enzyme having transcriptional repressor activity, or (b) a ubiquitin conjugating enzyme having transcriptional repressor activity and a mutated active site cysteine residue, whereby the mutated enzyme lacks ubiquitin conjugating activity, the included portion being at least about 12 amino acid residues in length and conferring the repressor activity on the protein, and
   a carrier, diluent or delivery agent.

39. A method for suppressing transcription in a eukaryotic cell in culture, the method comprising
   exposing the genome of the eukaryotic cell to a substantially purified protein, the protein having transcriptional repressor activity and having an amino acid sequence which includes at least a portion of the amino acid sequence of a ubiquitin conjugating enzyme having transcriptional repressor activity, the included portion being at least about 12 amino acid residues in length and conferring the repressor activity on the protein.

40. The method of claim 39 wherein the ubiquitin conjugating enzyme has a mutated active site cysteine residue, whereby the mutated enzyme lacks ubiquitin conjugating activity.

41. The method of claim 39 wherein the ubiquitin conjugating enzyme is a UBC-9.

42. The method of claim 39 wherein the genome is exposed to the protein by introducing a nucleic acid polymer which encodes the protein into the cell.

43. The method of claim 39 wherein the cell is transfected with a plasmid vector comprising a deoxyribonucleic acid polymer which encodes the protein.

44. The method of claim 39 wherein the cell is infected with a positive or negative sense virus having a genome comprising a nucleic acid polymer which encodes the protein.

45. The method of claim 39 wherein the genome is exposed to the protein by cotransfecting the cell with a deoxyribonucleic acid polymer which encodes the protein, and with a nucleic acid polymer which encodes WT1.

46. The method of claim 39 wherein the protein is a fusion protein comprising a DNA binding domain and transcriptional repressor domain, the transcriptional repressor domain having an amino acid sequence which includes at least a portion of the amino acid sequence of (a) a ubiquitin conjugating enzyme having transcriptional repressor activity or (b) a ubiquitin conjugating enzyme having transcriptional repressor activity and a mutated active site cysteine residue, whereby the mutated enzyme lacks ubiquitin conjugating activity, the included portion of the amino acid sequence being at least about 12 amino acid residues in length and conferring the repressor activity on the protein.

47. The method of claim 46 wherein the fusion protein comprises a Gal4 DNA binding domain.

48. The method of claim 39 wherein the cell is infected with a virus having a viral genome which includes a promoter having a TATA binding region, and wherein the protein is exposed to the viral genome, whereby transcription of the viral genome is repressed.

49. The method of claim 39 wherein the cell is a fungal cell.

50. The method of claim 39 wherein the cell is a yeast cell.

51. The method of claim 39 wherein the cell is a plant cell.

52. The method of claim 39 wherein the cell is a non-human animal cell.

53. The method of claim 39 wherein the cell is a non-human mammalian cell.

54. The method of claim 39 wherein the cell is a human cell.

55. The method of claim 54 wherein the human cell is exposed to the protein by contacting, infecting or transfecting the cell with a composition comprising a nucleic acid polymer which encodes the protein and an acceptable carrier, diluent or delivery agent.

56. The method of claim 54 wherein the human cell is a neoplastic tissue cell.

57. The method of claim 54 wherein the human cell is a Wilm's tumor cell.

58. The method of claim 39 wherein the genome is exposed to the protein by cotransfecting the cell with a deoxyribonucleic acid polymer encoding a transcriptional repressor protein, and with a deoxyribonucleic acid polymer encoding an adapter protein having transcriptional repressor activity and having an amino acid sequence which includes at least a portion of the amino acid sequence of a ubiquitin conjugating enzyme having transcriptional repressor activity, the included portion being at least about 12 amino acid residues in length and conferring the repressor activity on the adapter protein.

59. The method of claim 39 wherein the genome is exposed to a UBC-9 protein.

60. The method of claim 39 wherein the genome is exposed to hUBC-9.

61. The method of claim 39 wherein the genome comprises a deoxyribonucleic acid polymer which includes a promoter having a TATA binding region.

62. The method of claim 39 wherein the genome comprises a deoxyribonucleic acid polymer which includes a promoter selected from the group consisting of PDGF A-chain and SV40.

63. The method of claim 39 wherein the genome comprises a deoxyribonucleic acid polymer which includes a promoter selected from the group consisting of PDGF A-chain and SV40, and the gene is exposed to a UBC-9 protein.

64. A method for suppressing transcription in a eukaryotic cell in culture, the method comprising exposing the genome of the eukaryotic cell to a substantially purified protein having ubiquitin conjugating activity and transcriptional repressor activity, the protein having an amino acid sequence which includes at least a portion of the amino acid sequence of hUBC-9, SEQ ID NO: 3, the included portion being at least about 12 amino acid residues in length and conferring the repressor activity on the protein.

65. A method for suppressing transcription in a eukaryotic cell in vitro, the method comprising exposing the genome of the cell to a UBC-9 protein in vitro.

66. A method for suppressing transcription of a gene of a eukaryotic cell in culture, the method comprising transfecting the eukaryotic cell with a deoxyribonucleic acid polymer encoding a transcriptional repressor protein, and with a deoxyribonucleic acid polymer encoding an adapter protein having transcriptional repressor activity and having an amino acid sequence which includes at least a portion of the amino acid sequence of a ubiquitin conjugating enzyme having transcriptional repressor activity, the included portion being at least about 12 amino acid residues in length and conferring the repressor activity on the adapter protein.

67. A method for suppressing transcription of a gene of a eukaryotic cell in culture, the method comprising exposing the gene to a fusion protein comprising a DNA binding domain and transcriptional repressor domain, the transcriptional repressor domain having an amino acid sequence which includes at least a portion of the amino acid sequence of (a) a ubiquitin conjugating enzyme having transcriptional repressor activity or (b) a ubiquitin conjugating enzyme having transcriptional repressor activity and a mutated active site cysteine residue, whereby the mutated enzyme lacks ubiquitin conjugating activity, the included portion of the amino acid sequence being at least about 12 amino acid residues in length and conferring the repressor activity on the protein.

68. The method of claim 45 wherein the cell is transfected with a first vector comprising the deoxyribonucleic acid polymer which encodes the protein, and cotransfected with a second vector comprising the nucleic acid polymer which encodes WT1.

69. The method of claim 58 wherein the cell is transfected with a first vector comprising the deoxyribonucleic acid polymer encoding a transcriptional repressor protein, and cotransfected with a second vector comprising the deoxyribonucleic acid polymer encoding an adapter protein.

70. The method of claim 66 wherein the cell is transfected with a first vector comprising the deoxyribonucleic acid polymer encoding a transcriptional repressor protein, and cotransfected with a second vector comprising the deoxyribonucleic polymer encoding an adapter protein.

* * * * *

UNITED STATES PATENT AND TRADEMARK OFFICE
CERTIFICATE OF CORRECTION

PATENT NO. : 5,770,720
DATED : June 23, 1998
INVENTOR(S) : Thomas F. Deuel et al.

It is certified that error appears in the above-identified patent and that said Letters Patent is hereby corrected as shown below:

Column 2, line 52, after "SEQ ID NO: 1" insert --, Fig. 1A through Fig. 1C --.

Column 2, lines 52-53, after "SEQ ID NO: 2" insert --, Fig. 1B and Fig. 1C --.

Column 2, line 55, after "SEQ ID NO: 2" insert --, Fig. 1B and Fig. 1C --.

Column 5, line 38, replace "Fig. 1B" with -- Fig. 1D --.

Column 5, line 39, after "Fig. 1A" insert -- through Fig. 1C --.

Column 5, line 40, after "Fig. 1A" insert -- through Fig. 1C --.

Column 5, line 41, replace "and 1B" with -- through 1D --.

Column 5, line 42, replace "Figure 1A shows" with -- Figures 1A through 1C show --.

Column 5, line 49, replace "1B" with -- 1D --.

Column 8, line 66, replace "Figure 1A shows" with -- Figures 1A through 1C show --.

Column 9, line 8, replace "1B" with -- 1D --.

Column 10, line 22, replace "1B" with -- 1D --.

UNITED STATES PATENT AND TRADEMARK OFFICE
CERTIFICATE OF CORRECTION

PATENT NO. : 5,770,720
DATED : June 23, 1998
INVENTOR(S) : Thomas F. Deuel et al.

It is certified that error appears in the above-identified patent and that said Letters Patent is hereby corrected as shown below:

Column 21, line 62, after "Fig. 1A" insert -- through Fig. 1C --.

Signed and Sealed this

Twenty-third Day of March, 1999

Attest:

Q. TODD DICKINSON

*Attesting Officer*     *Acting Commissioner of Patents and Trademarks*